United States Patent
Belagaje et al.

(10) Patent No.: US 6,384,205 B1
(45) Date of Patent: May 7, 2002

(54) METABOTROPIC GLUTAMATE RECEPTOR 4 NUCLEIC ACID

(75) Inventors: Rama M. Belagaje; Su Wu, both of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 58 days.

(21) Appl. No.: 09/641,318

(22) Filed: Aug. 18, 2000

Related U.S. Application Data

(63) Continuation of application No. 08/816,178, filed on Mar. 12, 1997, now abandoned
(60) Provisional application No. 60/013,189, filed on Mar. 12, 1996.

(51) Int. Cl.$^7$ ......................... C12N 15/12; C07K 14/705
(52) U.S. Cl. ...................... 536/23.5; 536/23.1; 530/350
(58) Field of Search ............................... 536/23.5, 23.1; 530/350

(56) References Cited

FOREIGN PATENT DOCUMENTS

| WO | WO 9508627 A1 | * | 3/1995 |
| WO | WO 9522609 A2 | * | 8/1995 |

OTHER PUBLICATIONS

Y. Tanabe, et al., *The Journal of Neurosciene*, 13(4), pp. 1372–1378, Apr. 1993.

N. Okamoto, et al., *The American Society for Biochemistry and Molecular Biology, Inc.*, pp. 1231–1236, 1994.

K. Houamed, et al., *Science*, 252, pp. 1318–1321, Nat 31, 1991.

C. Thomsen, et al., *European Journal of Pharmacology*, 227, pp. 361–362, 1992.

Y. Tanabe et al., *Neuron*, 8, pp. 169–179, Jan. 1992.

S. Nakanishi. "Molecular Diversity of Glutamate Receptors and Implications for Brain Function." Science 259:597–603 (Oct. 23, 1992).

j.–p. Pin and R. Duvoisin. "The Metabotropic Glutamate Receptors: Structure and Functions." *Neuropharmacology* 34(1):1–26 (1995).

M. Hollmann and S. Heinemann. "Cloned Glutamate Receptors." *Annu. Rev. Neurosci.* 17:31–108 (1994).

P.J. Flor, et al. *Neuropharmacology* 34:149–155 (1995).

* cited by examiner

*Primary Examiner*—Lorraine Spector
*Assistant Examiner*—Claire M. Kaufman
(74) *Attorney, Agent, or Firm*—Alexander Wilson

(57) ABSTRACT

This invention describes a novel human glutamate receptors, designated mGluR4. This invention also encompasses nucleic acids encoding this receptor, or a fragment thereof, as well as methods employing this receptor and the nucleic acid compounds.

4 Claims, 1 Drawing Sheet

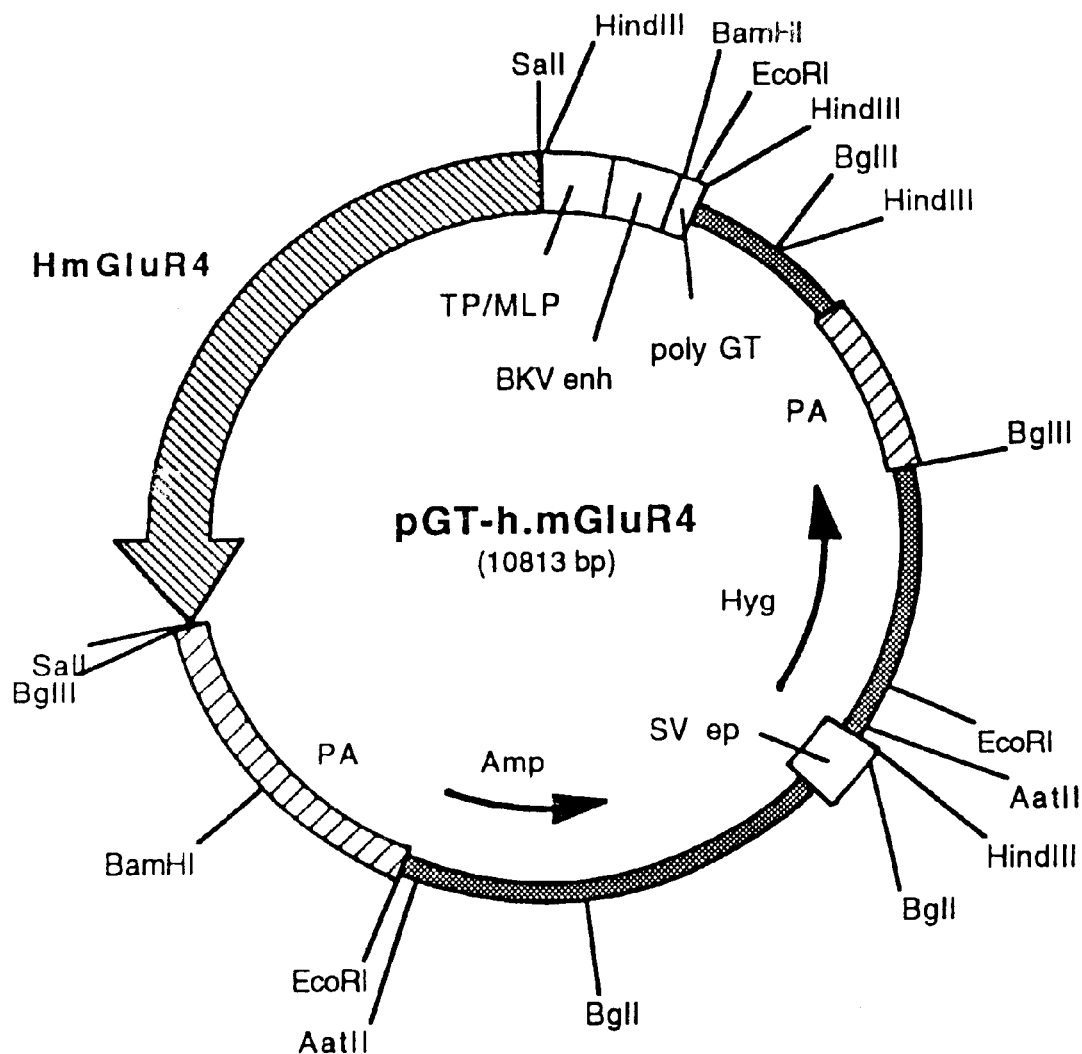

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 3431 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 26..2761

(xi) SEQUENCE DESCRIPTION: SEQ ID NO: 1:

```
TCATGGGTCT CTAGGCCTTT CCGAA ATG CCT GGG AAG AGA GGC TTG GGC TGG        52
                            Met Pro Gly Lys Arg Gly Leu Gly Trp
                             1               5

TGG TGG GCC CGG CTG CCC CTT TGC CTG CTC CTC AGC CTT TAC GGC CCC       100
Trp Trp Ala Arg Leu Pro Leu Cys Leu Leu Leu Ser Leu Tyr Gly Pro
 10              15                  20                  25

TGG ATG CCT TCC TCC CTG GGA AAG CCC AAA GGC CAC CCT CAC ATG AAT       148
Trp Met Pro Ser Ser Leu Gly Lys Pro Lys Gly His Pro His Met Asn
                 30                  35                  40

TCC ATC CGC ATA GAT GGG GAC ATC ACA CTG GGA GGC CTG TTC CCG GTG       196
Ser Ile Arg Ile Asp Gly Asp Ile Thr Leu Gly Gly Leu Phe Pro Val
             45                  50                  55

CAT GGC CGG GGC TCA GAG GGC AAG CCC TGT GGA GAA CTT AAG AAG GAA       244
His Gly Arg Gly Ser Glu Gly Lys Pro Cys Gly Glu Leu Lys Lys Glu
         60                  65                  70

AAG GGC ATC CAC CGG CTG GAG GCC ATG CTG TTC GCC CTG GAT CGC ATC       292
Lys Gly Ile His Arg Leu Glu Ala Met Leu Phe Ala Leu Asp Arg Ile
 75                  80                  85

AAC AAC GAC CCG GAC CTG CTG CCT AAC ATC ACG CTG GGC GCC CGC ATT       340
Asn Asn Asp Pro Asp Leu Leu Pro Asn Ile Thr Leu Gly Ala Arg Ile
 90                  95                 100                 105

CTG GAC ACC TGC TCC AGG GAC ACC CAT GCC CTC GAG CAG TCG CTG ACC       388
Leu Asp Thr Cys Ser Arg Asp Thr His Ala Leu Glu Gln Ser Leu Thr
                110                 115                 120

TTT GTG CAG GCG CTC ATC GAG AAG GAT GGC ACA GAG GTC CGC TGT GGC       436
Phe Val Gln Ala Leu Ile Glu Lys Asp Gly Thr Glu Val Arg Cys Gly
            125                 130                 135

AGT GGC GGC CCA CCC ATC ATC ACC AAG CCT GAA CGT GTG GTG GGT GTC       484
Ser Gly Gly Pro Pro Ile Ile Thr Lys Pro Glu Arg Val Val Gly Val
        140                 145                 150

ATC GGT GCT TCA GGG AGC TCG GTC TCC ATC ATG GTG GCC AAC ATC CTT       532
Ile Gly Ala Ser Gly Ser Ser Val Ser Ile Met Val Ala Asn Ile Leu
    155                 160                 165

CGC CTC TTC AAG ATA CCC CAG ATC AGC TAC GCC TCC ACA GCG CCA GAC       580
Arg Leu Phe Lys Ile Pro Gln Ile Ser Tyr Ala Ser Thr Ala Pro Asp
170                 175                 180                 185

CTG AGT GAC AAC AGC CGC TAC GAC TTC TTC TCC CGC GTG GTG CCC TCG       628
Leu Ser Asp Asn Ser Arg Tyr Asp Phe Phe Ser Arg Val Val Pro Ser
                190                 195                 200

GAC ACG TAC CAG GCC CAG GCC ATG GTG GAC ATC GTC CGC GCC CTC AAG       676
Asp Thr Tyr Gln Ala Gln Ala Met Val Asp Ile Val Arg Ala Leu Lys
            205                 210                 215
```

```
TGG AAC TAT GTG TCC ACA GTG GCC TCG GAG GGC AGC TAT GGT GAG AGC      724
Trp Asn Tyr Val Ser Thr Val Ala Ser Glu Gly Ser Tyr Gly Glu Ser
        220                 225                 230

GGT GTG GAG GCC TTC ATC CAG AAG TCC CGT GAG GAC GGG GGC GTG TGC      772
Gly Val Glu Ala Phe Ile Gln Lys Ser Arg Glu Asp Gly Gly Val Cys
    235                 240                 245

ATC GCC CAG TCG GTG AAG ATA CCA CGG GAG CCC AAG GCA GGC GAG TTC      820
Ile Ala Gln Ser Val Lys Ile Pro Arg Glu Pro Lys Ala Gly Glu Phe
250                 255                 260                 265

GAC AAG ATC ATC CGC CGC CTC CTG GAG ACT TCG AAC GCC AGG GCA GTC      868
Asp Lys Ile Ile Arg Arg Leu Leu Glu Thr Ser Asn Ala Arg Ala Val
                270                 275                 280

ATC ATC TTT GCC AAC GAG GAT GAC ATC AGG CGT GTG CTG GAG GCA GCA      916
Ile Ile Phe Ala Asn Glu Asp Asp Ile Arg Arg Val Leu Glu Ala Ala
                285                 290                 295

CGA AGG GCC AAC CAG ACA GGC CAT TTC TTC TGG ATG GGC TCT GAC AGC      964
Arg Arg Ala Asn Gln Thr Gly His Phe Phe Trp Met Gly Ser Asp Ser
        300                 305                 310

TGG GGC TCC AAG ATT GCA CCT GTG CTG CAC CTG GAG GAG GTG GCT GAG     1012
Trp Gly Ser Lys Ile Ala Pro Val Leu His Leu Glu Glu Val Ala Glu
    315                 320                 325

GGT GCT GTC ACG ATC CTC CCC AAG AGG ATG TCC GTA CGA GGC TTC GAC     1060
Gly Ala Val Thr Ile Leu Pro Lys Arg Met Ser Val Arg Gly Phe Asp
330                 335                 340                 345

CGC TAC TTC TCC AGC CGC ACG CTG GAC AAC AAC CGG CGC AAC ATC TGG     1108
Arg Tyr Phe Ser Ser Arg Thr Leu Asp Asn Asn Arg Arg Asn Ile Trp
                350                 355                 360

TTT GCC GAG TTC TGG GAG GAC AAC TTC CAC TGC AAG CTG AGC CGC CAC     1156
Phe Ala Glu Phe Trp Glu Asp Asn Phe His Cys Lys Leu Ser Arg His
                365                 370                 375

GCC CTC AAG AAG GGC AGC CAC GTC AAG AAG TGC ACC AAC CGT GAG CGA     1204
Ala Leu Lys Lys Gly Ser His Val Lys Lys Cys Thr Asn Arg Glu Arg
        380                 385                 390

ATT GGG CAG GAT TCA GCT TAT GAG CAG GAG GGG AAG GTG CAG TTT GTG     1252
Ile Gly Gln Asp Ser Ala Tyr Glu Gln Glu Gly Lys Val Gln Phe Val
    395                 400                 405

ATC GAT GCC GTG TAC GCC ATG GGC CAC GCG CTG CAC GCC ATG CAC CGT     1300
Ile Asp Ala Val Tyr Ala Met Gly His Ala Leu His Ala Met His Arg
410                 415                 420                 425

GAC CTG TGT CCC GGC CGC GTG GGG CTC TGC CCG CGC ATG GAC CCT GTA     1348
Asp Leu Cys Pro Gly Arg Val Gly Leu Cys Pro Arg Met Asp Pro Val
                430                 435                 440

GAT GGC ACC CAG CTG CTT AAG TAC ATC CGA AAC GTC AAC TTC TCA GGC     1396
Asp Gly Thr Gln Leu Leu Lys Tyr Ile Arg Asn Val Asn Phe Ser Gly
                445                 450                 455

ATC GCA GGG AAC CCT GTG ACC TTC AAT GAG AAT GGA GAT GCG CCT GGG     1444
Ile Ala Gly Asn Pro Val Thr Phe Asn Glu Asn Gly Asp Ala Pro Gly
        460                 465                 470

CGC TAT GAC ATC TAC CAA TAC CAG CTG CGC AAC GAT TCT GCC GAG TAC     1492
Arg Tyr Asp Ile Tyr Gln Tyr Gln Leu Arg Asn Asp Ser Ala Glu Tyr
    475                 480                 485

AAG GTC ATT GGC TCC TGG ACT GAC CAC CTG CAC CTT AGA ATA GAG CGG     1540
Lys Val Ile Gly Ser Trp Thr Asp His Leu His Leu Arg Ile Glu Arg
490                 495                 500                 505

ATG CAC TGG CCG GGG AGC GGG CAG CAG CTG CCC CGC TCC ATC TGC AGC     1588
Met His Trp Pro Gly Ser Gly Gln Gln Leu Pro Arg Ser Ile Cys Ser
                510                 515                 520

CTG CCC TGC CAA CCG GGT GAG CGG AAG AAG ACA GTG AAG GGC ATG CCT     1636
Leu Pro Cys Gln Pro Gly Glu Arg Lys Lys Thr Val Lys Gly Met Pro
```

```
                    525                 530                 535
TGC TGC TGG CAC TGC GAG CCT TGC ACA GGG TAC CAG TAC CAG GTG GAC       1684
Cys Cys Trp His Cys Glu Pro Cys Thr Gly Tyr Gln Tyr Gln Val Asp
            540                 545                 550

CGC TAC ACC TGT AAG ACG TGT CCC TAT GAC ATG CGG CCC ACA GAG AAC       1732
Arg Tyr Thr Cys Lys Thr Cys Pro Tyr Asp Met Arg Pro Thr Glu Asn
        555                 560                 565

CGC ACG GGC TGC CGG CCC ATC CCC ATC ATC AAG CTT GAG TGG GGC TCG       1780
Arg Thr Gly Cys Arg Pro Ile Pro Ile Ile Lys Leu Glu Trp Gly Ser
570                 575                 580                 585

CCC TGG GCC GTG CTG CCC CTC TTC CTG GCC GTG GTG GGC ATC GCT GCC       1828
Pro Trp Ala Val Leu Pro Leu Phe Leu Ala Val Val Gly Ile Ala Ala
                590                 595                 600

ACG TTG TTC GTG GTG ATC ACC TTT GTG CGC TAC AAC GAC ACG CCC ATC       1876
Thr Leu Phe Val Val Ile Thr Phe Val Arg Tyr Asn Asp Thr Pro Ile
            605                 610                 615

GTC AAG GCC TCG GGC CGT GAA CTG AGC TAC GTG CTG CTG GCA GGC ATC       1924
Val Lys Ala Ser Gly Arg Glu Leu Ser Tyr Val Leu Leu Ala Gly Ile
        620                 625                 630

TTC CTG TGC TAT GCC ACC ACC TTC CTC ATG ATC GCT GAG CCC GAC CTT       1972
Phe Leu Cys Tyr Ala Thr Thr Phe Leu Met Ile Ala Glu Pro Asp Leu
635                 640                 645

GGC ACC TGC TCG CTG CGC CGA ATC TTC CTG GGA CTA GGG ATG AGC ATC       2020
Gly Thr Cys Ser Leu Arg Arg Ile Phe Leu Gly Leu Gly Met Ser Ile
650                 655                 660                 665

AGC TAT GCA GCC CTG CTC ACC AAG ACC AAC CGC ATC TAC CGC ATC TTC       2068
Ser Tyr Ala Ala Leu Leu Thr Lys Thr Asn Arg Ile Tyr Arg Ile Phe
                670                 675                 680

GAG CAG GGC AAG CGC TCG GTC AGT GCC CCA CGC TTC ATC AGC CCC GCC       2116
Glu Gln Gly Lys Arg Ser Val Ser Ala Pro Arg Phe Ile Ser Pro Ala
            685                 690                 695

TCA CAG CTG GCC ATC ACC TTC AGC CTC ATC TCG CTG CAG CTG CTG GGC       2164
Ser Gln Leu Ala Ile Thr Phe Ser Leu Ile Ser Leu Gln Leu Leu Gly
        700                 705                 710

ATC TGT GTG TGG TTT GTG GTG GAC CCC TCC CAC TCG GTG GTG GAC TTC       2212
Ile Cys Val Trp Phe Val Val Asp Pro Ser His Ser Val Val Asp Phe
715                 720                 725

CAG GAC CAG CGG ACA CTC GAC CCC CGC TTC GCC AGG GGT GTG CTC AAG       2260
Gln Asp Gln Arg Thr Leu Asp Pro Arg Phe Ala Arg Gly Val Leu Lys
730                 735                 740                 745

TGT GAC ATC TCG GAC CTG TCG CTC ATC TGC CTG CTG GGC TAC AGC ATG       2308
Cys Asp Ile Ser Asp Leu Ser Leu Ile Cys Leu Leu Gly Tyr Ser Met
                750                 755                 760

CTG CTC ATG GTC ACG TGC ACC GTG TAT GCC ATC AAG ACA CGC GGC GTG       2356
Leu Leu Met Val Thr Cys Thr Val Tyr Ala Ile Lys Thr Arg Gly Val
            765                 770                 775

CCC GAG ACC TTC AAT GAG GCC AAG CCC ATT GGC TTC ACC ATG TAC ACC       2404
Pro Glu Thr Phe Asn Glu Ala Lys Pro Ile Gly Phe Thr Met Tyr Thr
        780                 785                 790

ACT TGC ATC GTC TGG CTG GCC TTC ATC CCC ATC TTC TTT GGC ACC TCG       2452
Thr Cys Ile Val Trp Leu Ala Phe Ile Pro Ile Phe Phe Gly Thr Ser
    795                 800                 805

CAG TCG GCC GAC AAG CTG TAC ATC CAG ACG ACG ACG CTG ACG GTC TCG       2500
Gln Ser Ala Asp Lys Leu Tyr Ile Gln Thr Thr Thr Leu Thr Val Ser
810                 815                 820                 825

GTG AGT CTG AGC GCC TCG GTG TCC CTG GGA ATG CTC TAC ATG CCC AAA       2548
Val Ser Leu Ser Ala Ser Val Ser Leu Gly Met Leu Tyr Met Pro Lys
                830                 835                 840

GTC TAC ATC ATC CTC TTC CAC CCG GAG CAG AAC GTG CCC AAG CGC AAG       2596
```

```
                                                                                2644
CGC AGC CTC AAA GCC GTC GTT ACG GCG GCC ACC ATG TCC AAC AAG TTC
Arg Ser Leu Lys Ala Val Val Thr Ala Ala Thr Met Ser Asn Lys Phe
        860                 865                 870

ACG CAG AAG GGC AAC TTC CGG CCC AAC GGA GAG GCC AAG TCT GAG CTC    2692
Thr Gln Lys Gly Asn Phe Arg Pro Asn Gly Glu Ala Lys Ser Glu Leu
    875                 880                 885

TGC GAG AAC CTT GAG GCC CCA GCG CTG GCC ACC AAA CAG ACT TAC GTC    2740
Cys Glu Asn Leu Glu Ala Pro Ala Leu Ala Thr Lys Gln Thr Tyr Val
890                 895                 900                 905

ACT TAC ACC AAC CAT GCA ATC TAGCGAGTCC ATGGAGCTGA GCAGCAGGAG       2791
Thr Tyr Thr Asn His Ala Ile
                910

GAGGAGCCGT GACCCTGTGG AAGGTGCGTC GGGCCAGGGC ACACCCAAG GGCCCAGCTG   2851

TCTTGCCTGC CCGTGGGCAC CCACGGACGT GGCTTGGTGC TGAGATAGCA GAGCCCCAG   2911

CCATCACTGC TGGCAGCCTG GGCAAACCGG GTGAGCAACA GGAGGACGAG GGGCCGGGGC  2971

GGTGCCAGGC TACCACAAGA ACCTGCGTCT TGGACCATTG CCCCTCCCGG CCCCAAACCA  3031

CAGGGGCTCA GGTCGTGTGG GCCCCAGTGC TAGATCTCTC CCTCCCTTCG TCTCTGTCTG  3091

TGCTGTTGGC GACCCCTCTG TCTGTCTCCA GCCCTGTCTT TCTGTTCTCT TATCTCTTTG  3151

TTTCACCTTT TCCCTCTCTG GCGTCCCCGG CTGCTTGTAC TCTTGGCCTT TTCTGTGTCT  3211

CCTTTCTGGC TCTTGCCTCC GCCTCTCTCT CTCATCCTCT TTGTCCTCAG CTCCTCCTGC  3271

TTTCTTGGGT CCCACCAGTG TCACTTTTCT GCCGTTTTCT TTCCTGTTCT CCTCTGCTTC  3331

ATTCTCGTCC AGCCATTGCT CCCCTCTCCC TGCCACCCTT CCCCAGTTCA CCAAACCTTA  3391

CATGTTGCAA AGAAAAAAAA AAAAAAGGAA TTCCTGCAGC                       3431

(2) INFORMATION FOR SEQ ID NO: 2:

(i) SEQUENCE CHARACTERISTICS:
        (A) LENGTH: 912 amino acids
        (B) TYPE: amino acid
        (D) TOPOLOGY: linear (ii) MOLECULE TYPE: protein (xi) SEQUENCE DESCRIPTION: SEQ ID NO: 2:

Met Pro Gly Lys Arg Gly Leu Gly Trp Trp Trp Ala Arg Leu Pro Leu
 1               5                  10                  15

Cys Leu Leu Leu Ser Leu Tyr Gly Pro Trp Met Pro Ser Ser Leu Gly
                20                  25                  30

Lys Pro Lys Gly His Pro His Met Asn Ser Ile Arg Ile Asp Gly Asp
            35                  40                  45

Ile Thr Leu Gly Gly Leu Phe Pro Val His Gly Arg Gly Ser Glu Gly
        50                  55                  60

Lys Pro Cys Gly Glu Leu Lys Lys Glu Lys Gly Ile His Arg Leu Glu
65                  70                  75                  80

Ala Met Leu Phe Ala Leu Asp Arg Ile Asn Asn Asp Pro Asp Leu Leu
                85                  90                  95

Pro Asn Ile Thr Leu Gly Ala Arg Ile Leu Asp Thr Cys Ser Arg Asp
                100                 105                 110

Thr His Ala Leu Glu Gln Ser Leu Thr Phe Val Gln Ala Leu Ile Glu
            115                 120                 125

Lys Asp Gly Thr Glu Val Arg Cys Gly Ser Gly Gly Pro Pro Ile Ile
        130                 135                 140
```

-continued

```
Thr Lys Pro Glu Arg Val Val Gly Val Ile Gly Ala Ser Gly Ser Ser
145                 150                 155                 160
Val Ser Ile Met Val Ala Asn Ile Leu Arg Leu Phe Lys Ile Pro Gln
            165                 170                 175
Ile Ser Tyr Ala Ser Thr Ala Pro Asp Leu Ser Asp Asn Ser Arg Tyr
        180                 185                 190
Asp Phe Phe Ser Arg Val Val Pro Ser Asp Thr Tyr Gln Ala Gln Ala
    195                 200                 205
Met Val Asp Ile Val Arg Ala Leu Lys Trp Asn Tyr Val Ser Thr Val
210                 215                 220
Ala Ser Glu Gly Ser Tyr Gly Glu Ser Gly Val Glu Ala Phe Ile Gln
225                 230                 235                 240
Lys Ser Arg Glu Asp Gly Gly Val Cys Ile Ala Gln Ser Val Lys Ile
                245                 250                 255
Pro Arg Glu Pro Lys Ala Gly Glu Phe Asp Lys Ile Ile Arg Arg Leu
            260                 265                 270
Leu Glu Thr Ser Asn Ala Arg Ala Val Ile Ile Phe Ala Asn Glu Asp
        275                 280                 285
Asp Ile Arg Arg Val Leu Glu Ala Ala Arg Arg Ala Asn Gln Thr Gly
    290                 295                 300
His Phe Phe Trp Met Gly Ser Asp Ser Trp Gly Ser Lys Ile Ala Pro
305                 310                 315                 320
Val Leu His Leu Glu Glu Val Ala Glu Gly Ala Val Thr Ile Leu Pro
                325                 330                 335
Lys Arg Met Ser Val Arg Gly Phe Asp Arg Tyr Phe Ser Ser Arg Thr
            340                 345                 350
Leu Asp Asn Asn Arg Arg Asn Ile Trp Phe Ala Glu Phe Trp Glu Asp
        355                 360                 365
Asn Phe His Cys Lys Leu Ser Arg His Ala Leu Lys Lys Gly Ser His
    370                 375                 380
Val Lys Lys Cys Thr Asn Arg Glu Arg Ile Gly Gln Asp Ser Ala Tyr
385                 390                 395                 400
Glu Gln Glu Gly Lys Val Gln Phe Val Ile Asp Ala Val Tyr Ala Met
                405                 410                 415
Gly His Ala Leu His Ala Met His Arg Asp Leu Cys Pro Gly Arg Val
            420                 425                 430
Gly Leu Cys Pro Arg Met Asp Pro Val Asp Gly Thr Gln Leu Leu Lys
        435                 440                 445
Tyr Ile Arg Asn Val Asn Phe Ser Gly Ile Ala Gly Asn Pro Val Thr
    450                 455                 460
Phe Asn Glu Asn Gly Asp Ala Pro Gly Arg Tyr Asp Ile Tyr Gln Tyr
465                 470                 475                 480
Gln Leu Arg Asn Asp Ser Ala Glu Tyr Lys Val Ile Gly Ser Trp Thr
                485                 490                 495
Asp His Leu His Leu Arg Ile Glu Arg Met His Trp Pro Gly Ser Gly
            500                 505                 510
Gln Gln Leu Pro Arg Ser Ile Cys Ser Leu Pro Cys Gln Pro Gly Glu
        515                 520                 525
Arg Lys Lys Thr Val Lys Gly Met Pro Cys Cys Trp His Cys Glu Pro
    530                 535                 540
Cys Thr Gly Tyr Gln Tyr Gln Val Asp Arg Tyr Thr Cys Lys Thr Cys
545                 550                 555                 560
```

-continued

```
Pro Tyr Asp Met Arg Pro Thr Glu Asn Arg Thr Gly Cys Arg Pro Ile
            565                 570                 575

Pro Ile Ile Lys Leu Glu Trp Gly Ser Pro Trp Ala Val Leu Pro Leu
            580                 585                 590

Phe Leu Ala Val Val Gly Ile Ala Ala Thr Leu Phe Val Val Ile Thr
            595                 600                 605

Phe Val Arg Tyr Asn Asp Thr Pro Ile Val Lys Ala Ser Gly Arg Glu
            610                 615                 620

Leu Ser Tyr Val Leu Leu Ala Gly Ile Phe Leu Cys Tyr Ala Thr Thr
625                 630                 635                 640

Phe Leu Met Ile Ala Glu Pro Asp Leu Gly Thr Cys Ser Leu Arg Arg
            645                 650                 655

Ile Phe Leu Gly Leu Gly Met Ser Ile Ser Tyr Ala Ala Leu Leu Thr
            660                 665                 670

Lys Thr Asn Arg Ile Tyr Arg Ile Phe Glu Gln Gly Lys Arg Ser Val
            675                 680                 685

Ser Ala Pro Arg Phe Ile Ser Pro Ala Ser Gln Leu Ala Ile Thr Phe
            690                 695                 700

Ser Leu Ile Ser Leu Gln Leu Leu Gly Ile Cys Val Trp Phe Val Val
705                 710                 715                 720

Asp Pro Ser His Ser Val Val Asp Phe Gln Asp Gln Arg Thr Leu Asp
            725                 730                 735

Pro Arg Phe Ala Arg Gly Val Leu Lys Cys Asp Ile Ser Asp Leu Ser
            740                 745                 750

Leu Ile Cys Leu Leu Gly Tyr Ser Met Leu Leu Met Val Thr Cys Thr
            755                 760                 765

Val Tyr Ala Ile Lys Thr Arg Gly Val Pro Glu Thr Phe Asn Glu Ala
            770                 775                 780

Lys Pro Ile Gly Phe Thr Met Tyr Thr Thr Cys Ile Val Trp Leu Ala
785                 790                 795                 800

Phe Ile Pro Ile Phe Phe Gly Thr Ser Gln Ser Ala Asp Lys Leu Tyr
            805                 810                 815

Ile Gln Thr Thr Thr Leu Thr Val Ser Val Ser Leu Ser Ala Ser Val
            820                 825                 830

Ser Leu Gly Met Leu Tyr Met Pro Lys Val Tyr Ile Ile Leu Phe His
            835                 840                 845

Pro Glu Gln Asn Val Pro Lys Arg Lys Arg Ser Leu Lys Ala Val Val
            850                 855                 860

Thr Ala Ala Thr Met Ser Asn Lys Phe Thr Gln Lys Gly Asn Phe Arg
865                 870                 875                 880

Pro Asn Gly Glu Ala Lys Ser Glu Leu Cys Glu Asn Leu Glu Ala Pro
            885                 890                 895

Ala Leu Ala Thr Lys Gln Thr Tyr Val Thr Tyr Thr Asn His Ala Ile
            900                 905                 910
```

(2) INFORMATION FOR SEQ ID NO: 3:

(i) SEQUENCE CHARACTERISTICS:
        (A) LENGTH: 3431 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO: 3:

-continued

```
UCAUGGGUCU CUAGGCCUUU CCGAAAUGCC UGGGAAGAGA GGCUUGGGCU GGUGGUGGGC      60

CCGGCUGCCC CUUUGCCUGC UCCUCAGCCU UUACGGCCCC UGGAUGCCUU CCUCCCUGGG     120

AAAGCCCAAA GGCCACCCUC ACAUGAAUUC CAUCCGCAUA GAUGGGGACA UCACACUGGG     180

AGGCCUGUUC CCGGUGCAUG GCCGGGCUCC AGAGGGCAAG CCCUGUGGAG AACUUAAGAA     240

GGAAAAGGGC AUCCACCGGC UGGAGGCCAU GCUGUUCGCC CUGGAUCGCA UCAACAACGA     300

CCCGGACCUG CUGCCUAACA UCACGCUGGG CGCCCGCAUU CUGGACACCU GCUCCAGGGA     360

CACCCAUGCC CUCGAGCAGU CGCUGACCUU UGUGCAGGCG CUCAUCGAGA GGAUGGCAC      420

AGAGGUCCGC UGUGGCAGUG GCGGCCCACC CAUCAUCACC AAGCCUGAAC GUGUGGUGGG     480

UGUCAUCGGU GCUUCAGGGA GCUCGGUCUC CAUCAUGGUG GCCAACAUCC UUCGCCUCUU     540

CAAGAUACCC CAGAUCAGCU ACGCCUCCAC AGCGCCAGAC CUGAGUGACA ACAGCCGCUA     600

CGACUUCUUC UCCCGCGUGG UGCCCUCGGA CACGUACCAG GCCCAGGCCA UGGUGGACAU     660

CGUCCGCGCC CUCAAGUGGA ACUAUGUGUC CACAGUGGCC UCGGAGGGCA GCUAUGGUGA     720

GAGCGGUGUG GAGGCCUUCA UCCAGAAGUC CCGUGAGGAC GGGGGCGUGU GCAUCGCCCA     780

GUCGGUGAAG AUACCACGGG AGCCCAAGGC AGGCGAGUUC GACAAGAUCA UCCGCCGCCU     840

CCUGGAGACU CGAACGCCA GGGCAGUCAU CAUCUUUGCC AACGAGGAUG ACAUCAGGCG     900

UGUGCUGGAG GCAGCACGAA GGGCCAACCA GACAGGCCAU UUCUUCUGGA UGGGCUCUGA     960

CAGCUGGGGC UCCAAGAUUG CACCUGUGCU GCACCUGGAG GAGGUGGCUG AGGGUGCUGU    1020

CACGAUCCUC CCCAAGAGGA UGUCCGUACG AGGCUUCGAC CGCUACUUCU CCAGCCGCAC    1080

GCUGGACAAC AACCGGCGCA ACAUCUGGUU UGCCGAGUUC UGGGAGGACA ACUUCCACUG    1140

CAAGCUGAGC CGCCACGCCC UCAAGAAGGG CAGCCACGUC AAGAAGUGCA CCAACCGUGA    1200

GCGAAUUGGG CAGGAUUCAG CUUAUGAGCA GGAGGGGAAG GUGCAGUUUG UGAUCGAUGC    1260

CGUGUACGCC AUGGGCCACG CGCUGCACGC CAUGCACCGU GACCUGUGUC CCGGCCGCGU    1320

GGGGCUCUGC CCGCGCAUGG ACCCUGUAGA UGGCACCCAG CUGCUUAAGU ACAUCCGAAA    1380

CGUCAACUUC UCAGGCAUCG CAGGGAACCC UGUGACCUUC AAUGAGAAUG GAGAUGCGCC    1440

UGGGCGCUAU GACAUCUACC AAUACCAGCU GCGCAACGAU UCUGCCGAGU ACAAGGUCAU    1500

UGGCUCCUGG ACUGACCACC UGCACCUUAG AAUAGAGCGG AUGCACUGGC CGGGGAGCGG    1560

GCAGCAGCUG CCCCGCUCCA UCUGCAGCCU GCCCUGCCAA CCGGGUGAGC GGAAGAAGAC    1620

AGUGAAGGGC AUGCCUUGCU GCUGGCACUG CGAGCCUUGC ACAGGGUACC AGUACCAGGU    1680

GGACCGCUAC ACCUGUAAGA CGUGUCCCUA UGACAUGCGG CCCACAGAGA ACCGCACGGG    1740

CUGCCGGCCC AUCCCCAUCA UCAAGCUUGA GUGGGGCUCG CCCUGGGCCG UGCUGCCCCU    1800

CUUCCUGGCC GUGGUGGGCA UCGCUGCCAC GUUGUUCGUG GUGAUCACCU UUGUGCGCUA    1860

CAACGACACG CCCAUCGUCA AGGCCUCGGG CCGUGAACUG AGCUACGUGC UGCUGGCAGG    1920

CAUCUUCCUG UGCUAUGCCA CCACCUUCCU CAUGAUCGCU GAGCCCGACC UUGGCACCUG    1980

CUCGCUGCGC CGAAUCUUCC UGGGACUAGG GAUGAGCAUC AGCUAUGCAG CCCUGCUCAC    2040

CAAGACCAAC CGCAUCUACC GCAUCUUCGA GCAGGGCAAG CGCUCGGUCA GUGCCCCACG    2100

CUUCAUCAGC CCCGCCUCAC AGCUGGCCAU CACCUUCAGC CUCAUCUCGC UGCAGCUGCU    2160

GGGCAUCUGU GUGUGGUUUG UGGUGGACCC CUCCCACUCG GUGGUGGACU UCCAGGACCA    2220

GCGGACACUC GACCCCCGCU UCGCCAGGGG UGUGCUCAAG UGUGACAUCU CGGACCUGUC    2280

GCUCAUCUGC CUGCUGGGCU ACAGCAUGCU GCUCAUGGUC ACGUGCACCG UGUAUGCCAU    2340

CAAGACACGC GGCGUGCCCG AGACCUUCAA UGAGGCCAAG CCCAUUGGCU UCACCAUGUA    2400
```

-continued

```
CACCACUUGC AUCGUCUGGC UGGCCUUCAU CCCCAUCUUC UUUGGCACCU CGCAGUCGGC      2460

CGACAAGCUG UACAUCCAGA CGACGACGCU GACGGUCUCG GUGAGUCUGA GCGCCUCGGU      2520

GUCCCUGGGA AUGCUCUACA UGCCCAAAGU CUACAUCAUC CUCUUCCACC CGGAGCAGAA      2580

CGUGCCCAAG CGCAAGCGCA GCCUCAAAGC CGUCGUUACG GCGGCCACCA UGUCCAACAA      2640

GUUCACGCAG AAGGGCAACU UCCGGCCCAA CGGAGAGGCC AAGUCUGAGC UCUGCGAGAA      2700

CCUUGAGGCC CCAGCGCUGG CCACCAAACA GACUUACGUC ACUUACACCA ACCAUGCAAU      2760

CUAGCGAGUC CAUGGAGCUG AGCAGCAGGA GGAGGAGCCG UGACCCUGUG GAAGGUGCGU      2820

CGGGCCAGGG CCACACCCAA GGGCCCAGCU GUCUUGCCUG CCCGUGGGCA CCCACGGACG      2880

UGGCUUGGUG CUGAGAUAGC AGAGCCCCCA GCCAUCACUG CUGGCAGCCU GGGCAAACCG      2940

GGUGAGCAAC AGGAGGACGA GGGGCCGGGG CGGUGCCAGG CUACCACAAG AACCUGCGUC      3000

UUGGACCAUU GCCCCUCCCG GCCCCAAACC ACAGGGCUC AGGUCGUGUG GGCCCCAGUG       3060

CUAGAUCUCU CCCUCCCUUC GUCUCUGUCU GUGCUGUUGG CGACCCCUCU GUCUGUCUCC     3120

AGCCCUGUCU UUCUGUUCUC UUAUCUCUUU GUUUCACCUU UUCCCUCUCU GGCGUCCCCG     3180

GCUGCUUGUA CUCUUGGCCU UUUCUGUGUC UCCUUCUGG CUCUUGCCUC CGCCUCUCUC      3240

UCUCAUCCUC UUUGUCCUCA GCUCCUCCUG CUUUCUUGGG UCCACCAGU GUCACUUUUC      3300

UGCCGUUUUC UUUCCUGUUC UCCUCUGCUU CAUUCUCGUC CAGCCAUUGC UCCCCUCUCC     3360

CUGCCACCCU UCCCCAGUUC ACCAAACCUU ACAUGUUGCA AAGAAAAAA AAAAAAGGA       3420

AUUCCUGCAG C                                                         3431
```

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

```
GGCTGGGCCT GGTGGTGGGC YMGGCTNCC                                       29
```

(2) INFORMATION FOR SEQ ID NO: 5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

```
TGGMAARCCC AAGGGYCAYC CCCAYATG                                        28
```

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

```
GGTGATSATG GGSGGGCCSC CNGWNCC                                    27
```

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

```
CACCTCCTCM AGSCKCAGCA CRGGNGC                                    27
```

(2) INFORMATION FOR SEQ ID NO: 8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

```
TTGATGTGGC TKCCCTTCTT SAGNGCRTG                                  29
```

(2) INFORMATION FOR SEQ ID NO: 9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
GGGGACATCA CACTGGGAGG CCTGT                                      25
```

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
CAGCGGACCT CTGTGCCATC CTTCT                                      25
```

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
CCCTCACTAA AGGGAACAAA AGCT                                       24
```

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CCCCTCGAGG TCGACGGTAT CGAT                                        24

(2) INFORMATION FOR SEQ ID NO: 13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

CAGCGGACCT CTGTGCCATC CTTCT                                     25

(2) INFORMATION FOR SEQ ID NO: 14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

GGGCTCGAGG TCGACGGGTC TCTAGGCCTT TCCG                          34

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

GAGCAGGTGT CCAGAATGCG GGCGCCC                                  27

(2) INFORMATION FOR SEQ ID NO: 16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

GTAATACGAC TCACTATAGG GC                                        22

(2) INFORMATION FOR SEQ ID NO: 17:

(i) SEQUENCE CHARACTERISTICS:
        (A) LENGTH: 21 base pairs

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CACAGGGCTT GCCCTCTGAG C                                           21

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

CGGGTCGACG GGTCTCTAGG CCTTTC                                      26

(2) INFORMATION FOR SEQ ID NO: 19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

GATCTGTCGA CA                                                     12

(2) INFORMATION FOR SEQ ID NO: 20:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

ACAGCTGTCT AG                                                     12

(2) INFORMATION FOR SEQ ID NO: 21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

GAGCAGGTGT CCAGAATGCG GGCGCCC                                     27

(2) INFORMATION FOR SEQ ID NO: 22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear
```

(ii) MOLECULE TYPE: cDNA (xi) SEQUENCE DESCRIPTION: SEQ ID NO: 22:

GTCTGGCTGG CCTTCATCCC CATC                                                    24

(2) INFORMATION FOR SEQ ID NO: 23:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 23:

GTCACACCAC AGAAGTAAGG TTCCTTCAC                                                29

(2) INFORMATION FOR SEQ ID NO: 24:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 24:

CCTCACTCTC TTCCGCATCG CTGTCTGCGA                                               30

US 6,384,205 B1

METABOTROPIC GLUTAMATE RECEPTOR 4 NUCLEIC ACID

This application is a continuation application and claims the benefit under 35 U.S.C. 120 of parent U.S. application Ser. No. 08/816,178, filed Mar. 12, 1997, abandoned, which, in turn, claims the benefit under 35 U.S.C. 119(e) of U.S. Provisional Application No. 60/013,189, filed Mar. 12, 1996.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology*, 21:165 (1981); Monaghan, Bridges, and Cotman, *Annual Reviews in Pharmacology and Toxicology*, 29:365 (1989); Watkins, Krogsgaard-Larsen, and Honore, *Transactions in Pharmaceutical Science*, 11:25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), a-amino-3-hydroxy-5-methylisoxazole-4-propionic acid (AMPA), and kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, or changes in ion channel function. Schoepp and Conn, *Trends in Pharmacological Science*, 14:13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacological Science*, 11:508 (1990); McDonald and Johnson, *Brain Research Reviews*, 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Agonists and antagonists of these receptors may be useful for the treatment of acute and chronic neurodegenerative conditions, and as antipsychotic, anticonvulsant, analgesic, anxiolytic, antidepressant, and anti-emetic agents.

The present invention provides an additional human excitatory amino acid receptor, designated mGluR4, to those previously known. The characterization and treatment of physiological disorders is hereby furthered.

SUMMARY OF THE INVENTION

This invention provides an isolated amino acid compound useful as a human metabotropic glutamate receptor, the compound having the amino acid sequence which is designated as SEQ ID NO:2.

The present invention also provides an isolated nucleic acid compound that comprises a nucleic acid sequence which encodes for the amino acid compounds provided. Particularly this invention provides the isolated nucleic acid compound having the sequence designated as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and reaction profile of agents useful in the treatment or prevention of disorders associated with an excess or deficiency in the amount of glutamate present.

BRIEF DESCRIPTION OF THE DRAWING

FIG. 1 is a restriction and functional map of the plasmid pGT-h-mGluR4.

DETAILED DESCRIPTION OF THE INVENTION

The terms and abbreviations used in this document have their normal meanings unless otherwise designated. For example "_C" refers to degrees Celsius; "N" refers to normal or normality; "mmol" refers to millimole or millimoles; "g" refers to gram or grams; "ml" means milliliter or milliliters; "M" refers to molar or molarity; "$\mu$g" refers to microgram or micrograms; and "$\mu$l" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides urodine, cytidine, guanosine, and adenosine, respectively when they occur in RNA molecules. In double stranded DNA, base pair may refer to a pairing of A with T or C with G. In a DNA/RNA, heteroduplex base pair may refer to a pairing of A with U or C with G. (See the definition of "complementary", infra.)

The terms "cleavage" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature. "Ligation" refers to the process of forming phosphodiester bonds between two nucleic acid fragments (T. Maniatis, et al., supra., p. 146). Unless otherwise provided, ligation may be accomplished using known buffers and conditions with a DNA ligase, such as TY DNA ligase.

The term "plasmid" refers to an extrachromosomal (usually) self-replicating genetic element. Plasmids are generally designated by a lower case "p" followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A frameshift mutation occurs when a base pair is inserted or deleted from a DNA segment. When this occurs, the result is a different protein from that coded for by the DNA segment prior to the frameshift mutation. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter and other regulatory elements to control transcription of the inserted DNA.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and eelectroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells with polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by joining DNA molecules from different sources. The term "vector" as used herein includes Recombinant DNA cloning vectors and Recombinant DNA expression vectors.

The terms "complementary" or "complementarity" as used herein refers to the pairing of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid hybridization with another nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other glutamate receptor subtypes. This term may also be employed in the sense that such antibodies may be used to differentiate between the human mGluR4 receptor protein and analogous proteins derived from other species.

The term "PCR" as used herein refers to the widely-known polymerase chain reaction employing a thermally-stable polymerase.

The present invention provides an isolated amino acid compound useful as a human metabotropic glutamate receptor. The compound comprises the amino acid sequence:

```
Met Pro Gly Lys Arg Gly Leu Gly Trp Trp Ala Arg Leu Pro Leu
 1               5                  10                 15

Cys Leu Leu Ser Leu Tyr Gly Pro Trp Met Pro Ser Ser Leu Gly
             20                  25                 30

Lys Pro Lys Gly His Pro His Met Asn Ser Ile Arg Ile Asp Gly Asp
             35                  40                 45

Ile Thr Leu Gly Gly Leu Phe Pro Val His Gly Arg Gly Ser Glu Gly
         50                  55                 60

Lys Pro Cys Gly Glu Leu Lys Lys Glu Lys Gly Ile His Arg Leu Glu
 65              70                  75                 80

Ala Met Leu Phe Ala Leu Asp Arg Ile Asn Asn Asp Pro Asp Leu Leu
             85                  90                 95

Pro Asn Ile Thr Leu Cly Ala Arg Ile Leu Asp Thr Cys Ser Arg Asp
             100                 105                110

Thr His Ala Leu Glu Gln Ser Leu Thr Phe Val Gln Ala Leu Ile Glu
             115                 120                125

Lys Asp Gly Thr Glu Val Arg Cys Gly Ser Gly Gly Pro Pro Ile Ile
             130                 135                140

Thr Lys Pro Glu Arg Val Val Gly Val Ile Gly Ala Ser Gly Ser Ser
145                 150                 155                160

Val Ser Ile Met Val Ala Asn Ile Leu Arg Leu Phe Lys Ile Pro Gln
                 165                 170                175

Ile Ser Tyr Ala Ser Thr Ala Pro Asp Leu Ser Asp Asn Ser Arg Tyr
             180                 185                 190

Asp Phe Phe Ser Arg Val Val Pro Ser Asp Thr Tyr Gln Ala Gln Ala
             195                 200                 205

Met Val Asp Ile Val Arg Ala Leu Lys Trp Asn Tyr Val Ser Thr Val
210                 215                 220

Ala Ser Glu Gly Ser Tyr Gly Glu Ser Gly Val Glu Ala Phe Ile Gln
225                 230                 235                240

Lys Ser Arg Glu Asp Gly Gly Val Cys Ile Ala Gln Ser Val Lys Ile
                 245                 250                 255

Pro Arg Glu Pro Lys Ala Gly Glu Phe Asp Lys Ile Ile Arg Arg Leu
                 260                 265                 270

Leu Glu Thr Ser Asn Ala Arg Ala Val Ile Ile Phe Ala Asn Glu Asp
                 275                 280                 285

Asp Ile Arg Arg Val Leu Glu Ala Ala Arg Arg Ala Asn Gln Thr Gly
                 290                 295                 300

His Phe Phe Trp Met Gly Ser Asp Ser Trp Gly Ser Lys Ile Ala Pro
305                 310                 315                 320

Val Leu His Leu Glu Glu Val Ala Glu Gly Ala Val Thr Ile Leu Pro
                 325                 330                 335

Lys Arg Met Ser Val Arg Gly Phe Asp Arg Tyr Phe Ser Ser Arg Thr
                 340                 345                 350

Leu Asp Asn Asn Arg Arg Asn Ile Trp Phe Ala Glu Phe Trp Glu Asp
                 355                 360                 365

Asn Phe His Cys Lys Leu Ser Arg His Ala Leu Lys Lys Gly Ser His
                 370                 375                 380

Val Lys Lys Cys Thr Asn Arg Glu Arg Ile Gly Gln Asp Ser Ala Tyr
385                 390                 395                 400

Glu Gln Glu Gly Lys Val Gln Phe Val Ile Asp Ala Val Tyr Ala Met
                 405                 410                 415
```

-continued

```
Gly His Ala Leu His Ala Met His Arg Asp Leu Cys Pro Gly Arg Val
            420                 425                 430

Gly Leu Cys Pro Arg Met Asp Pro Val Asp Gly Thr Gln Leu Leu Lys
            435                 440                 445

Tyr Ile Arg Asn Val Asn Phe Ser Gly Ile Ala Gly Asn Pro Val Thr
450                 455                 460

Phe Asn Glu Asn Gly Asp Ala Pro Gly Arg Tyr Asp Ile Tyr Gln Tyr
465                 470                 475                 480

Gln Leu Arg Asn Asp Ser Ala Glu Tyr Lys Val Ile Gly Ser Trp Thr
            485                 490                 495

Asp His Leu His Leu Arg Ile Glu Arg Met His Trp Pro Gly Ser Gly
            500                 505                 510

Gln Gln Leu Pro Arg Ser Ile Cys Ser Leu Pro Cys Gln Pro Gly Glu
            515                 520                 525

Arg Lys Lys Thr Val Lys Gly Met Pro Cys Cys Trp His Cys Glu Pro
            530                 535                 540

Cys Thr Gly Tyr Gln Tyr Gln Val Asp Arg Tyr Thr Cys Lys Thr Cys
545                 550                 555                 560

Pro Tyr Asp Met Arg Pro Thr Glu Asn Arg Thr Gly Cys Arg Pro Ile
            565                 570                 575

Pro Ile Ile Lys Leu Glu Trp Gly Ser Pro Trp Ala Val Leu Pro Leu
            580                 585                 590

Phe Leu Ala Val Val Gly Ile Ala Ala Thr Leu Phe Val Val Ile Thr
            595                 600                 605

Phe Val Arg Tyr Asn Asp Thr Pro Ile Val Lys Ala Ser Gly Arg Glu
            610                 615                 620

Leu Ser Tyr Val Leu Leu Ala Gly Ile Phe Leu Cys Tyr Ala Thr Thr
625                 630                 635                 640

Phe Leu Met Ile Ala Glu Pro Asp Leu Gly Thr Cys Ser Leu Arg Arg
            645                 650                 655

Ile Phe Leu Gly Leu Gly Met Ser Ile Ser Tyr Ala Ala Leu Leu Thr
            660                 665                 670

Lys Thr Asn Arg Ile Tyr Arg Ile Phe Glu Gln Gly Lys Arg Ser Val
            675                 680                 685

Ser Ala Pro Arg Phe Ile Ser Pro Ala Ser Gln Leu Ala Ile Thr Phe
690                 695                 700

Ser Leu Ile Ser Leu Gln Leu Leu Gly Ile Cys Val Trp Phe Val Val
705                 710                 715                 720

Asp Pro Ser His Ser Val Val Asp Phe Gln Asp Gln Arg Thr Leu Asp
            725                 730                 735

Pro Arg Phe Ala Arg Gly Val Leu Lys Cys Asp Ile Ser Asp Leu Ser
            740                 745                 750

Leu Ile Cys Leu Leu Gly Tyr Ser Met Leu Leu Met Val Thr Cys Thr
            755                 760                 765

Val Tyr Ala Ile Lys Thr Arg Gly Val Pro Glu Thr Phe Asn Glu Ala
770                 775                 780

Lys Pro Ile Gly Phe Thr Met Tyr Thr Thr Cys Ile Val Trp Leu Ala
785                 790                 795                 800

Phe Ile Pro Ile Phe Phe Gly Thr Ser Gln Ser Ala Asp Lys Leu Tyr
            805                 810                 815

Ile Gln Thr Thr Thr Leu Thr Val Ser Val Ser Leu Ser Ala Ser Val
            820                 825                 830

Ser Leu Gly Met Leu Tyr Met Pro Lys Val Tyr Ile Ile Leu Phe His
            835                 840                 845
```

```
Pro Glu Gln Asn Val Pro Lys Arg Lys Arg Ser Leu Lys Ala Val Val
    850                 855                 860

Thr Ala Ala Thr Met Ser Asn Lys Phe Thr Gln Lys Gly Asn Phe Arg
865                 870                 875                 880

Pro Asn Gly Glu Ala Lys Ser Glu Leu Cys Glu Asn Leu Glu Ala Pro
                885                 890                 895

Ala Leu Ala Thr Lys Gln Fhr Tyr Val Thr Tyr Thr Asn His Ala Ile
            900                 905                 910
``` which is hereinafter designated as SEQ ID NO:2.

The present invention also provides an isolated nucleic acid compound that comprises a nucleic acid sequence which encodes for the amino acid compounds provided. Particularly, this invention provides the isolated nucleic acid compound having the sequence:

```
TCATGGGTCT CTAGGCCTTT CCGAA ATG CCT GGG AAG AGA GGC TTG GGC TGG         52
                             Met Pro Gly Lys Arg Gly Leu Gly Trp
                              1               5

TGG TGG GCC CGG CTG CCC CTT TGC CTG CTC CTC AGC CTT TAC GGC CCC        100
Trp Trp Ala Arg Leu Pro Leu Cys Leu Leu Leu Ser Leu Tyr Gly Pro
 10              15                  20                  25

TGG ATG CCT TCC TCC CTG GGA AAG CCC AAA GGC CAC CCT CAC ATG AAT        148
Trp Met Pro Ser Ser Leu Gly Lys Pro Lys Gly His Pro His Met Asn
                 30                  35                  40

TCC ATC CGC ATA GAT GGG GAC ATC ACA CTG GGA GGC CTG TTC CCG GTG        196
Ser Ile Arg Ile Asp Gly Asp Ile Thr Leu Gly Gly Leu Phe Pro Val
             45                  50                  55

CAT GGC CGG GGC TCA GAG GGC AAG CCC TGT GGA GAA CTT AAG AAG GAA        244
His Gly Arg Gly Ser Glu Gly Lys Pro Cys Gly Glu Leu Lys Lys Glu
             60                  65                  70

AAG GGC ATC CAC CGG CTG GAG GCC ATG CTG TTC GCC CTG GAT CGC ATC        292
Lys Gly Ile His Arg Leu Glu Ala Met Leu Phe Ala Leu Asp Arg Ile
 75                  80                  85

AAC AAC GAC CCG GAC CTG CTG CCT AAC ATC ACG CTG GGC GCC CGC ATT        340
Asn Asn Asp Pro Asp Leu Leu Pro Asn Ile Thr Leu Gly Ala Arg Ile
 90                  95                 100                 105

CTG GAC ACC TGC TCC AGG GAC ACC CAT GCC CTC GAG CAG TCG CTG ACC        388
Leu Asp Thr Cys Ser Arg Asp Thr His Ala Leu Glu Gln Ser Leu Thr
                110                 115                 120

TTT GTG CAG GCG CTC ATC GAG AAG GAT GGC ACA GAG GTC CGC TGT GGC        436
Phe Val Gln Ala Leu Ile Glu Lys Asp Gly Thr Glu Val Arg Cys Gly
            125                 130                 135

AGT GGC GGC CCA ccC ATC ATC ACC AAG CCT GAA CGT GTG GTG GGT GTC        484
Ser Gly Gly Pro Pro Ile Ile Thr Lys Pro Glu Arg Val Val Gly Val
            140                 145                 150

ATC GGT GCT TCA GGG AGC TCG GTC TCC ATC ATG GTG GCC AAC ATC CTT        532
Ile Gly Ala Ser Gly Ser Ser Val Ser Ile Met Val Ala Asn Ile Leu
 155                 160                 165

CGC CTC TTC AAG ATA CCC CAG ATC AGC TAC GCC TCC ACA GCG CCA GAC        580
Arg Leu Phe Lys Ile Pro Gln Ile Ser Tyr Ala Ser Thr Ala Pro Asp
170                 175                 180                 185

CTG AGT GAC AAC AGC CGC TAC GAC TTC TTC TCC CGC GTG GTG CCC TCG        628
Leu Ser Asp Asn Ser Arg Tyr Asp Phe Phe Ser Arg Val Val Pro Ser
                190                 195                 200

GAC ACG TAC CAG GCC CAG GCC ATG GTG GAC ATC GTC CGC GCC CTC AAG        676
Asp Thr Tyr Gln Ala Gln Ala Met Val Asp Ile Val Arg Ala Leu Lys
            205                 210                 215

TGG AAC TAT GTG TCC ACA GTG GCC TCG GAG GGC AGC TAT GGT GAG AGC        724
Trp Asn Tyr Val Ser Thr Val Ala Ser Glu Gly Ser Tyr Gly Glu Ser
            220                 225                 230
```

-continued

```
GGT GTG GAG GCC TTC ATC CAG AAG TCC CGT GAG GAC GGG GGC GTG TGC      772
Gly Val Glu Ala Phe Ile Gln Lys Ser Arg Glu Asp Gly Gly Val Cys
235                 240                 245

ATC GCC CAG TCG GTG AAG ATA CCA CGG GAG CCC AAG GCA GGC GAG TTC      820
Ile Ala Gln Ser Val Lys Ile Pro Arg Glu Pro Lys Ala Gly Glu Phe
250                 255                 260                 265

GAC AAG ATC ATC CGC CGC CTC CTG GAG ACT TCG AAC GCC AGG GCA GTC      868
Asp Lys Ile Ile Arg Arg Leu Leu Glu Thr Ser Asn Ala Arg Ala Val
                270                 275                 280

ATC ATC TTT GCC AAC GAG GAT GAC ATC AGG CGT GTG CTG GAG GCA GCA      916
Ile Ile Phe Ala Asn Glu Asp Asp Ile Arg Arg Val Leu Glu Ala Ala
            285                 290                 295

CGA AGG GCC AAC CAG ACA GGC CAT TTC TTC TGG ATG GGC TCT GAC AGC      964
Arg Arg Ala Asn Gln Thr Gly His Phe Phe Trp Met Gly Ser Asp Ser
        300                 305                 310

TGG GGC TCC AAG ATT GCA CCT GTG CTG CAC CTG GAG GAG GTG GCT GAG     1012
Trp Gly Ser Lys Ile Ala Pro Val Leu His Leu Glu Glu Val Ala Glu
315                 320                 325

GGT GCT GTC ACG ATC CTC CCC AAG AGG ATG TCC GTA CGA GGC TTC GAC     1060
Gly Ala Val Thr Ile Leu Pro Lys Arg Met Ser Val Arg Gly Phe Asp
330                 335                 340                 345

CGC TAC TTC TCC AGC CGC ACG CTG GAC AAC AAC CGG CGC AAC ATC TGG     1108
Arg Tyr Phe Ser Ser Arg Thr Leu Asp Asn Asn Arg Arg Asn Ile Trp
                350                 355                 360

TTT GCC GAG TTC TGG GAG GAC AAC TTC CAC TGC AAG CTG AGC CGC CAC     1156
Phe Ala Glu Phe Trp Glu Asp Asn Phe His Cys Lys Leu Ser Arg His
            365                 370                 375

GCC CTC AAG AAG GGC AGC CAC GTC AAG AAG TGC ACC AAC CGT GAG CGA     1204
Ala Leu Lys Lys Gly Ser His Val Lys Lys Cys Thr Asn Arg Glu Arg
        380                 385                 390

ATT GGG CAG GAT TCA GCT TAT GAG CAG GAG GGG AAG GTG CAG TTT GTG     1252
Ile Gly Gln Asp Ser Ala Tyr Glu Gln Glu Gly Lys Val Gln Phe Val
    395                 400                 405

ATC GAT GCC GTG TAC GCC ATG GGC CAC GCG CTG CAC GCC ATG CAC CGT     1300
Ile Asp Ala Val Tyr Ala Met Gly His Ala Leu His Ala Met His Arg
410                 415                 420                 425

GAC CTG TGT CCC GGC CGC GTG GGG CTC TGC CCG CGC ATG GAC CCT GTA     1348
Asp Leu Cys Pro Gly Arg Val Gly Leu Cys Pro Arg Met Asp Pro Val
                430                 435                 440

GAT GGC ACC CAG CTG CTT AAG TAC ATC CGA AAC GTC AAC TTC TCA GGC     1396
Asp Gly Thr Gln Leu Leu Lys Tyr Ile Arg Asn Val Asn Phe Ser Gly
            445                 450                 455

ATC GCA GGG AAC CCT GTG ACC TTC AAT GAG AAT GGA GAT GCG CCT GGG     1444
Ile Ala Gly Asn Pro Val Thr Phe Asn Glu Asn Gly Asp Ala Pro Gly
        460                 465                 470

CGC TAT GAC ATC TAC CAA TAC CAG CTG CGC AAC GAT TCT GCC GAG TAC     1492
Arg Tyr Asp Ile Tyr Gln Tyr Gln Leu Arg Asn Asp Ser Ala Glu Tyr
    475                 480                 485

AAG GTC ATT GGC TCC TGG ACT GAC CAC CTG CAC CTT AGA ATA GAG CGG     1540
Lys Val Ile Gly Ser Trp Thr Asp His Leu His Leu Arg Ile Glu Arg
490                 495                 500                 505

ATG CAC TGG CCG GGG AGC GGG CAG CAG CTG CCC CGC TCC ATC TGC AGC     1588
Met His Trp Pro Gly Ser Gly Gln Gln Leu Pro Arg Ser Ile Cys Ser
                510                 515                 520

CTG CCC TGC CAA CCG GGT GAG CGG AAG AAG ACA GTG AAG GGC ATG CCT     1636
Leu Pro Cys Gln Pro Gly Glu Arg Lys Lys Thr Val Lys Gly Met Pro
            525                 530                 535

TGC TGC TGG CAC TGC GAG CCT TGC ACA GGG TAC CAG TAC CAG GTG GAC     1684
Cys Cys Trp His Cys Glu Pro Cys Thr Gly Tyr Gln Tyr Gln Val Asp
        540                 545                 550
```

```
CGC TAC ACC TGT AAG ACG TGT CCC TAT GAC ATG CGG CCC ACA GAG AAC    1732
Arg Tyr Thr Cys Lys Thr Cys Pro Tyr Asp Met Arg Pro Thr Glu Asn
    555                 560                 565

CGC ACG GGC TGC CGG CCC ATC CCC ATC ATC AAG CTT GAG TGG GGC TCG    1780
Arg Thr Gly Cys Arg Pro Ile Pro Ile Ile Lys Leu Glu Trp Gly Ser
570                 575                 580                 585

CCC TGG GCC GTG CTG CCC CTC TTC CTG GCC GTG GTG GGC ATC GCT GCC    1828
Pro Trp Ala Val Leu Pro Leu Phe Leu Ala Val Val Gly Ile Ala Ala
                590                 595                 600

ACG TTG TTC GTG GTG ATC ACC TTT GTG CGC TAC AAC GAC ACG CCC ATC    1876
Thr Leu Phe Val Val Ile Thr Phe Val Arg Tyr Asn Asp Thr Pro Ile
            605                 610                 615

GTC AAG GC& TCG GGC CGT GAA CTG AGC TAC GTG CTG CTG GCA GGC ATC    1924
Val Lys Ala Ser Gly Arg Glu Leu Ser Tyr Val Leu Leu Ala Gly Ile
        620                 625                 630

TTC CTG TGC TAT GCC ACC ACC TTC CTC ATG ATC GCT GAG CCC GAC CTT    1972
Phe Leu Cys Tyr Ala Thr Thr Phe Leu Met Ile Ala Glu Pro Asp Leu
    635                 640                 645

GGC ACC TGC TCG CTG CGC CGA ATC TTC CTG GGA CTA GGG ATG AGC ATC    2020
Gly Thr Cys Ser Leu Arg Arg Ile Phe Leu Gly Leu Gly Met Ser Ile
650                 655                 660                 665

AGC TAT GCA GCC CTG CTC ACC AAG ACC AAC CGC ATC TAC CGC ATC TTC    2068
Ser Tyr Ala Ala Leu Leu Thr Lys Thr Asn Arg Ile Tyr Arg Ile Phe
                670                 675                 680

GAG CAG GGC AAG CGC TCG GTC AGT GCC CCA CGC TTC ATC AGC CCC GCC    2116
Glu Gln Gly Lys Arg Ser Val Ser Ala Pro Arg Phe Ile Ser Pro Ala
            685                 690                 695

TCA CAG CTG GCC ATC ACC TTC AGC CTC ATC TCG CTG CAG CTG CTG GGC    2164
Ser Gln Leu Ala Ile Thr Phe Ser Leu Ile Ser Leu Gln Leu Leu Gly
        700                 705                 710

ATC TGT GTG TGG TTT GTG GTG GAC CCC TCC CAC TCG GTG GTG GAC TTC    2212
Ile Cys Val Trp Phe Val Val Asp Pro Ser His Ser Val Val Asp Phe
    715                 720                 725

CAG GAC CAG CGG ACA CTC GAC CCC CGC TTC GCC AGG GGT GTG CTC AAG    2260
Gln Asp Gln Arg Thr Leu Asp Pro Arg Phe Ala Arg Gly Val Leu Lys
730                 735                 740                 745

TGT GAC ATC TCG GAC CTG TCG CTC ATC TGC CTG CTG GGC TAC AGC ATG    2308
Cys Asp Ile Ser Asp Leu Ser Leu Ile Cys Leu Leu Gly Tyr Ser Met
                750                 755                 760

CTG CTC ATG GTC ACG TGC ACC GTG TAT GCC ATC AAG ACA CGC GGC GTG    2356
Leu Leu Met Val Thr Cys Thr Val Tyr Ala Ile Lys Thr Arg Gly Val
            765                 770                 775

CCC GAG ACC TTC AAT GAG GCC AAG CCC ATT GGC TTC ACC ATG TAC ACC    2404
Pro Glu Thr Phe Asn Glu Ala Lys Pro Ile Gly Phe Thr Met Tyr Thr
        780                 785                 790

ACT TGC ATC GTC TGG CTG GCC TTC ATC CCC ATC TTC TTT GGC ACC TCG    2452
Thr Cys Ile Val Trp Leu Ala Phe Ile Pro Ile Phe Phe Gly Thr Ser
    795                 800                 805

CAG TCG GCC GAC AAG CTG TAC ATC CAG ACG ACG ACG CTG ACG GTC TCG    2500
Gln Ser Ala Asp Lys Leu Tyr Ile Gln Thr Thr Thr Leu Thr Val Ser
810                 815                 820                 825

GTG AGT CTG AGC GCC TCG GTG TCC CTG GGA ATG CTC TAC ATG CCC AAA    2548
Val Ser Leu Ser Ala Ser Val Ser Leu Gly Met Leu Tyr Met Pro Lys
                830                 835                 840

GTC TAC ATC ATC CTC TTC CAC CCG GAG CAG AAC GTG CCC AAG CGC AAG    2596
Val Tyr Ile Ile Leu Phe His Pro Glu Gln Asn Val Pro Lys Arg Lys
            845                 850                 855

CGC AGC CTC AAA GCC GTC GTT ACG GCG GCC ACC ATG TCC AAC AAG TTC    2644
Arg Ser Leu Lys Ala Val Val Thr Ala Ala Thr Met Ser Asn Lys Phe
        860                 865                 870
```

-continued

```
ACG CAG AAG GGC AAC TTC CGG CCC AAC GGA GAG GCC AAG TCT GAG CTC    2692
Thr Gln Lys Gly Asn Phe Arg Pro Asn Gly Glu Ala Lys Ser Glu Leu
    875                 880                 885

TGC GAG AAC CTT GAG GCC CCA GCG CTG GCC ACC AAA CAG ACT TAC GTC    2740
Cys Glu Asn Leu Glu Ala Pro Ala Leu Ala Thr Lys Gln Thr Tyr Val
890                 895                 900                 905

ACT TAC ACC AAC CAT GCA ATC TAGCGAGTCC ATGGAGCTGA GCAGCAGGAG       2791
Thr Tyr Thr Asn His Ala Ile
                910

GAGGAGCCGT GACCCTGTGG AAGGTGCGTC GGGCCAGGGC CACACCCAAG GGCCCAGCTG  2851

TCTTGCCTGC CCGTGGGCAC CCACGGACGT GGCTTGGTGC TGAGATAGCA GAGCCCCCAG  2911

CCATCACTGC TGGCAGCCTG GGCAAACCGG GTGAGCAACA GGAGGACGAG GGGCCGGGGC  2971

GGTGCCAGGC TACCACAAGA ACCTGCGTCT TGGACCATTG CCCCTCCCGG CCCCAAACCA  3031

CAGGGGCTCA GGTCGTGTGG GCCCCAGTGC TAGATCTCTC CCTCCCTTCG TCTCTGTCTG  3091

TGCTGTTGGC GACCCCTCTG TCTGTCTCCA GCCCTGTCTT TCTGTTCTCT TATCTCTTTG  3151

TTTCACCTTT TCCCTCTCTG GCGTCCCCGG CTGCTTGTAC TCTTGGCCTT TTCTGTGTCT  3211

CCTTTCTGGC TCTTGCCTCC GCCTCTCTCT CTCATCCTCT TTGTCCTCAG CTCCTCCTGC  3271

TTTCTTGGGT CCCACCACTG TCACTTTTCT GCCGTTTTCT TTCCTGTTCT CCTCTGCTTC  3331

ATTCTCGTCC AGCCATTGCT CCCCTCTCCC TGCCACCCTT CCCCAGTTCA CCAAACCTTA  3391

CATGTTGCAA AAGAAAAAAA AAAAAAGGAA TTCCTGCAGC                       3431
``` which is hereinafter designated as SEQ ID NO:1.

The present invention provides the protein of SEQ ID NO:2, a human metabotropic glutamate receptor, designated as a mGluR4 receptor using the nomenclature system described in D.D. Schoepp, "Glutamate receptors", *Handbook of Receptors and Channels*, Chapter 13 (S. J. Peroutka, ed., CRC Press, 1984). Based on the rat cognate of this receptor, the mGluR4 receptor is believed to be found throughout many regions of the brain. More specifically, expression of the receptor is found in the neurons of the rat brain. High levels of message expression of the receptor are found in the olfactory bulb, thalamus, cerebellum, and lateral septum. See Tanabe et al., *J. Neuroscience*, Vol. 13, pp. 1372–78 (1993). This receptor is believed to potentiate central nervous system responses and is, therefore, an important target for pharmaceutical purposes.

Skilled artisans will recognize that the proteins of the present invention can be isolated from brain tissue or synthesized by a number of different methods. All of the amino acid compounds of the invention can be made by chemical methods well known in the art, including solid phase peptide synthesis, or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, N.Y., pgs. 54–92. For example, peptides may be synthesized by solid-phase methodology utilizing an Applied Biosystems 430A peptide synthesizer (commercially available from Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl
Asp, cyclohexyl
Glu, cyclohexyl
Ser, Benzyl
Thr, Benzyl
Tyr, 4-bromo carbobenzoxy Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celsius or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in E. L. Brown, et al., *Methods in Enzymology*, 68:109–151 (1979). See also, J. Sambrook, et al., supra.

The basic steps in the recombinant production of desired proteins are:

a) construction of a natural, synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences and constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
| --- | --- |
| DH5α | F⁻ (φ80dlacZΔM15), Δ(lacZYA-argF)U169 supE44, λ⁻, hsdR17($r_K^-$, $m_K$+), recA1, endA1, gyrA96, thi-1, relA1 |
| HB101 | supE44, hsdS20($r_B^-$ $m_B^-$), recA13, ara-14, proA2 lacY1, galK2, rpsL20, xy1–5, mt1-1, mcrB, mrr |
| JM109 | recA1, e14⁻(mcrA), supE44, endA1, hsdR17($r_K^-$, $m_K^+$), gyrA96, relA1, thi-1, AE(lac-proAB), F' [traD36, proAB+ lacI$^q$, lacZ AE15] |
| RR1 | supE44, hsdS20($r_B^-$ $m_B^-$), ara-14 proA2, lacY1, galK2, rpsL20, xy1–5, mt1–5 |
| χ1776 | F⁻, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ⁻ |
| 294 | endA, thi⁻, hsr⁻, hsm$_k^+$ (U.S. Pat. 4,366,246) |
| XL1 Blue | recA1, endA1, gyrA96, thi, hsdR17($r_k$, $m_k$+), supE44, relA1, λ–, AE(lac), [F', proAB, laclqZAEM15, Tn10 (tet$^R$)] |

These strains are all commercially available from suppliers such as: Bethesda Research Laboratories, Gaithersburg, Maryland 20877 and Stratagene Cloning Systems, La Jolla, Calif. 92037; or are readily available to the public from sources such as the American Type Culture Collection, 10801 University Boulevard, Manassas, Va. 20110-2209, Except where otherwise noted, these bacterial strains can be used interchangeably. The genotypes listed are illustrative of many of the desired characteristics for choosing a bacterial host and are not meant to limit the invention in any way or manner. The genotype designations are in accordance with standard nomenclature. See, for example, J. Sambrook, et al., supra.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., *Nature* (*London*), 275:615 (1978); and Goeddel et al., *Nature* (*London*), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in *Protein Purification: From Molecular Mechanisms to Large Scale Processes*, American Chemical Society, Washington, D.C. (1990).

In addition to cloning and expressing the genes of interest in the prokaryotic systems as discussed above, the proteins of the present invention may also be produced in eukaryotic systems. The present invention is not limited to use in any particular eukaryotic host cell but may instead be used in an assortment of eukaryotic host cells. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed in Table I below:

TABLE 1

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPM18226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

A preferred cell line employed in this invention is the widely available cell line AV12-664 (hereinafter referred to as "AV12"). This cell line is available from the American Type Culture Collection under the accession number ATCC CRL 9595. The AV12 cell line was derived by injecting a Syrian hamster in the scruff of the neck with human adenovirus 12 and then isolating and culturing cells from the resulting tumor.

Cell lines, such as AV12, produce glutamate endogenously. As a result, substantial amounts of glutamate are secreted into the culture medium thereby making it somewhat difficult to express and study glutamate receptors due to the activation of the transfected receptor. Mechanisms such as the use of an effective glutamate transport system can be employed to remove excess glutmate effectively.

Therefore, a more preferred cell line for use in the present invention is the cell line RGT-18 (hereinafter referred to as "RGT"). The RGT cell line is constructed by transfecting the cell line AV12 with an expression plasmid in which the rat glutamate transporter gene (GLAST) is expressed. By using this cell line, the glutamate level in 24 hour medium of RGT is reduced to less than 3 micromolar, thus reducing the basal activation and/or desensitization of the receptor or the requirement for extensive washing to remove residual glutamate before assay procedures. See Storck, et al, *Proc. Nat'l Acad. Sci. USA*, 89:10955–59 (November 1992) and Desai et al, *Molecular Pharmacology*, 48:648–657 (1995).

A wide variety of vectors, some of which are discussed below, exist for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

A preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A(E1A) gene product. The E1A gene product (actually, the E1A gene produces two products, which are collectively referred to herein as "the E1A gene product") is an immediate-early gene product of adenovirus, a large DNA virus.

An especially preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and U.S. Pat. No. 4,992,373, issued Feb. 12, 1991, as well as co-pending U.S. patent application Ser. No. 07/368,700 and EPO Publication Number 245 949, published on Nov. 19, 1987, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which allows for the insertion of the gene encoding the protein of interest. The skilled artisan understands that linkers or adapters may be employed in cloning the gene of interest into this BclI site.

An even more preferred expression vector is the plasmid pGT-h. The pGT-h plasmid contains a unique BclI site which allows for the insertion of a gene encoding the protein of interest and also contains a gene encoding the hygromycin resistance determinant. The skilled artisan understands that linkers or adapters may be employed in cloning the gene of interest into this BclI site. Plasmid pGT-h contains the following elements beginning at the EcoRl site and proceeding counterclockwise: the EcoRl to blunt-ended NdeI fragment of pBR322 containing the ampicillin resistant gene and origin of replicaiton; the PvuII to blunt-ended BamHI fragment of pSV2-hyg' [derivative of pSV2-hyg constructed by A. Smith and P. Berg] containing a hygromycin phosphotransferase (HyPR) expression cistron; the blunt-ended NdeI (nt 2297) to AccI (nt 2246) restriction fragment of pBR322; the AccI (nt 4339) to StuI (nt 5122) restriction fragment of BKV-P2; the GBMT HindIII promoter cassette; HindIII and BclI linker; the 610 bp MhoI fragment of simian virus 40 (SV40) containing a splice junction; the 988 bp BclI to EcoRI fragment of SV40 containing the polyadenylation signal. See Berg, et al, *Biotechnigues*, 14:972–978 (1993).

The pGT-h series of plasmids functions most efficiently when introduced into a host cell which produces the E1A gene product, cell lines such as AV12-664, RGT-18, 293 cells, and others, described supra. The construction and method of using the pGT-h plasmid is described in detail in Berg et al., supra, European Patent Application Publication 0445939 published on Sep. 11, 1991 and U.S. patent application Ser. No. 08/446,126, filed May 19, 1995, incorporated herein by reference. Plasmid pGT-h can be isolated from *E. coli* K12 AG1/pGT-h, which is deposited with the Northern Regional Research Laboratory under accession number NRRL B-18592.

Transfection of the mammalian cells with vectors can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenoviruses, the adeno-associated viruses, the vaccinia virus, the herpes viruses, the baculoviruses, and the rous sarcoma virus are useful. Such a method is described in U.S. Pat. No. 4,775,624, incorporated herein by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which may be functional equivalents of the protein of SEQ ID NO:2 are shown in Table II, infra.

TABLE II

| Original Residue | Exemplary Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human glutamate mGluR4 receptor molecule may be produced using synthetic methodology. This synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See, e.g., M. J. Gait, ed., *Oligonucleotide Synthesis, A Practical Approach*, (1984).]

The synthetic human glutamate mGluR4 receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the mGluR4 receptor molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence:

```
UCAUGGGUCU CUAGGCCUUU CCGAAAUGCC UGGGAAGAGA GGCUUGGGCU GGUGGUGGGC      60

CCGGCUGCCC CUUUGCCUGC UCCUCAGCCU UUACGGCCCC UGGAUGCCUU CCUCCCUGGG     120

AAAGCCCAAA GGCCACCCUC ACAUGAAUUC CAUCCGCAUA GAUGGGGACA UCACACUGGG     180

AGGCCUGUUC CCGGUGCAUG GCCGGGGCUC AGAGGGCAAG CCCUGUGGAG AACUUAAGAA     240

GGAAAAGGGC AUCCACCGGC UGGAGGCCAU GCUGUUCGCC CUGGAUCGCA UCAACAACGA     300

CCCGGACCUG CUGCCUAACA UCACGCUGGG CGCCCGCAUU CUGGACACCU GCUCCAGGGA     360

CACCCAUGCC CUCGAGCAGU CGCUGACCUU UGUGCAGGCG CUCAUCGAGA AGGAUGGCAC     420

AGAGGUCCGC UGUGGCAGUG GCGGCCCACC CAUCAUCACC AAGCCUGAAC GUGUGGUGGG     480

UGUCAUCGGU GCUUCAGGGA GCUCGGUCUC CAUCAUGGUG GCCAACAUCC UUCGCCUCUU     540

CAAGAUACCC CAGAUCAGCU ACGCCUCCAC AGCGCCAGAC CUGAGUGACA ACAGCCGCUA     600

CGACUUCUUC UCCCGCGUGG UGCCCUCGGA CACGUACCAG GCCCAGGCCA UGGUGGACAU     660

CGUCCGCGCC CUCAAGUGGA ACUAUGUGUC CACAGUGGCC UCGGAGGGCA GCUAUGGUGA     720

GAGCGGUGUG GAGGCCUUCA UCCAGAAGUC CCGUGAGGAC GGGGGCGUGU GCAUCGCCCA     780

GUCGGUGAAG AUACCACGGG AGCCCAAGGC AGGCGAGUUC GACAAGAUCA UCCGCCGCCU     840

CCUGGAGACU UCGAACGCCA GGGCAGUCAU CAUCUUUGCC AACGAGGAUG ACAUCAGGCG     900

UGUGCUGGAG GCAGCACGAA GGGCCAACCA GACAGGCCAU UUCUUCUGGA UGGGCUCUGA     960

CAGCUGGGGC UCCAAGAUUG CACCUGUGCU GCACCUGGAG GAGGUGGCUG AGGGUGCUGU    1020

CACGAUCCUC CCCAAGAGGA UGUCCGUACG AGGCUUCGAC CGCUACUUCU CCAGCCGCAC    1080

GCUGGACAAC AACCGGCGCA ACAUCUGGUU UGCCGAGUUC UGGGAGGACA ACUUCCACUG    1140

GCGAAUUGGG CAGGAUUCAG CUUAUGAGCA GGAGGGGAAG GUGCAGUUUG UGAUCGAUGC    1260

CGUGUACGCC AUGGGCCACG CGCUGCACGC CAUGCACCGU GACCUGUGUC CCGGCCGCGU    1320

GGGGCUCUGC CCGCGCAUGG ACCCUGUAGA UGGCACCCAG CUGCUUAAGU ACAUCCGAAA    1380

CGUCAACUUC UCAGGCAUCG CAGGGAACCC UGUGACCUUC AAUGAGAAUG GAGAUGCGCC    1440

UGGGCGCUAU GACAUCUACC AAUACCAGCU GCGCAACGAU UCUGCCGAGU ACAAGGUCAU    1500

UGGCUCCUGG ACUGACCACC UGCACCUUAG AAUAGAGCGG AUGCACUGGC CGGGGAGCGG    1560

GCAGCAGCUG CCCCGCUCCA UCUGCAGCCU GCCCUGCCAA CCGGGUGAGC GGAAGAAGAC    1620
```

-continued

```
AGUGAAGGGC AUGCCUUGCU GCUGGCACUG CGAGCCUUGC ACAGGGUACC AGUACCAGGU  1680

GGACCGCUAC ACCUGUAAGA CGUGUCCCUA UGACAUGCGG CCCACAGAGA ACCGCACGGG  1740

CUGCCGGCCC AUCCCCAUCA UqAAGCUUGA GUGGGGCUCG CCCUGGGCCG UGCUGCCCCU  1800

CUUCCUGGCC GUGGUGGGCA UCGCUGCCAC GUUGUUCGUG GUGAUCACCU UUGUGCGCUA  1860

CAACGACACG CCCAUCGUCA AGGCCUCGGG CCGUGAACUG AGCUACGUGC UGCUGGCAGG  1920

CAUCUUCCUG UGCUAUGCCA CCACCUUCCU CAUGAUCGCU GAGCCCGACC UUGGCACCUG  1980

CUCGCUGCGC CGAAUCUUCC UGGGACUAGG GAUGAGCAUC AGCUAUGCAG CCCUGCUCAC  2040

CAAGACCAAC CGCAUCUACC GCAUCUUCGA GCAGGGCAAG CGCUCGGUCA GUGCCCCACG  2100

CUUCAUCAGC CCCGCCUCAC AGCUGGCCAU CACCUUCAGC CUCAUCUCGC UGCAGCUGCU  2160

GGGCAUCUGU GUGUGGUUUG UGGUGGACCC CUCCCACUCG GUGGUGGACU UCCAGGACCA  2220

GCGGACACUC GACCCCCGCU UCGCCAGGGG UGUGCUCAAG UGUGACAUCU CGGACCUGUC  2280

GCUCAUCUGC CUGCUGGGCU ACAGCAUGCU GCUCAUGGUC ACGUGCACCG UGUAUGCCAU  2340

CAAGACACG GGCGUGCCCG AGACCUUCAA UGAGGCCAAG CCCAUUGGCU UCACCAUGUA  2400

CACCACUUGC AUCGUCUGGC UGGCCUUCAU CCCCAUCUUC UUUGGCACCU CGCAGUCGGC  2460

CGACAAGCUG UACAUCCAGA CGACGACGCU GACGGUCUCG GUGAGUCUGA GCGCCUCGGU  2520

GUCCCUGGGA AUGCUCUACA UGCCCAAAGU CUACAUCAUC CUCUUCCACC CGGAGCAGAA  2580

CGUGCCCAAG CGCAAGCGCA GCCUCAAAGC CGUCGUUACG GCGGCCACCA UGUCCAACAA  2640

GUUCACGCAG AAGGGCAACU UCCGGCCCAA CGGAGAGGCC AAGUCUGAGC UCUGCGAGAA  2700

CCUUGAGGCC CCAGCGCUGG CCACCAAACA GACUUACGUC ACUUACACCA ACCAUGCAAU  2760

CUAGCGAGUC CAUGGAGCUG AGCAGCAGGA GGAGGAGCCG UGACCCUGUG GAAGGUGCGU  2820

CGGGCCAGGG CCACACCCAA GGGCCCAGCU GUCUUGCCUG CCCGUGGGCA CCCACGGACG  2880

UGGCUUGGUG CUGAGAUAGC AGAGCCCCCA GCCAUCACUG CUGGCAGCCU GGGCAAACCG  2940

GGUGAGCAAC AGGAGGACGA GGGGCCGGGG CGGUGCCAGG CUACCACAAG AACCUGCGUC  3000

UUGGACCAUU GCCCCUCCCG GCCCCAAACC ACAGGGCUC AGGUCGUGUG GGCCCCAGUG  3060

CUAGAUCUCU CCCUCCCUUC GUCUCUGUCU GUGCUGUUGG CGACCCCUCU GUCUGUCUCC  3120

AGCCCUGUCU UUCUGUUCUC UUAUCUCUUU GUUUCACCUU UUCCCUCUCU GGCGUCCCCG  3180

GCUGCUUGUA CUCUUGGCCU UUUCUGUGUC UCCUUUCUGG CUCUUGCCUC CGCCUCUCUC  3240

UCUCAUCCUC UUUGUCCUCA GCUCCUCCUG CUUUCUUGGG UCCACCAGU GUCACUUUUC  3300

UGCCGUUUUC UUUCCUGUUC UCCUCUGCUU CAUUCUCGUC CAGCCAUUGC UCCCCUCUCC  3360

CUGCCACCCU UCCCCAGUUC ACCAAACCUU ACAUGUUGCA AAAGAAAAAA AAAAAAGGA   3420

AUUCCUGCAG C                                                     3431
``` hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to human genomic DNA or messenger RNA encoding a human glutamate receptor, is provided. Preferably, the compound is DNA.

The term "selectively hybridize" as used herein may refer to either of two situations. In the first such embodiment of this invention, the nucleic acid compounds described supra hybridize to a human glutamate receptor under more stringent hybridization conditions than these same nucleic acid compounds would hybridize to an analogous glutamate receptor of another species, e.g. rodent. In the second such embodiment of this invention, these probes hybridize to the mGluR4 receptor under more stringent hybridization conditions than other related compounds, including nucleic acid sequences encoding other glutamate receptors.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1. Plasmid pGT-h.mGluR4, is an especially preferred DNA vector of the present invention.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The plasmid of the present invention can be readily modified to construct expression vectors that produce mGluR4 receptors in a variety of organisms, including, for example, E. coli, Sf9 (as host for baculovirus), Spodoptera and Saccharomyces.

One of the most widely employed techniques for altering a nucleic acid sequence is by way of oligonucleotide-directed site-specific mutagenesis. B. Comack, "Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for E. coli can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and E. coli cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is RGT-18. The preferred vector for expression is one which comprises SEQ ID NO:1. Another preferred host cell for this method is E. coli. An especially preferred expression vector in E. coli is one which comprises SEQ ID NO:1. Transformed host cells may be cultured under conditions well known to skilled artisans such that SEQ ID NO:2 is expressed, thereby producing mGluR4 in the recombinant host cell.

The ability of glutamate to bind to the mGluR4 receptor is essential in the development of a multitude of indications. In developing agents which act as antagonists or agonists of the mGluR4 receptor, it would be desirable, therefore, to determine those agents which bind the mGluR4 receptor. Generally, such an assay includes a method for determining whether a substance is a functional ligand of the mGluR4 receptor, said method comprising contacting a functional compound of the mGluR4 receptor with said substance, monitoring binding activity by physically detectable means, and identifying those substances which effect a chosen response. Preferably, the physically detectable means is competition with labeled glutamate or binding of ligand in an oocyte transient expression system The instant invention provides such a screening system useful for discovering agents which compete with glutamate for binding to the mGluR4 receptor, said screening system comprising the steps of:

a) preparing a human mGluR4 receptor;
b) exposing said human mGluR4 receptor to a potential inhibitor or surrogate of the glutamate/mGluR4 receptor complex;
c) introducing glutamate;
d) removing non-specifically bound molecules; and
e) quantifying the concentration of bound potential inhibitor and/or glutamate.

This allows one to rapidly screen for inhibitors or surrogates of the formation of the glutamate/mGluR4 receptor complex. Utilization of the screening system described above provides a sensitive and rapid means to determine compounds which interfere with the formation of the glutamate/mGluR4 receptor complex. This screening system may also be adapted to automated procedures such as a PANDEX® (Baxter-Dade Diagnostics) system allowing for efficient high-volume screening of potential therapeutic agents.

In such a screening protocol a mGluR4 receptor is prepared as elsewhere described herein, preferably using recombinant DNA technology. A sample of a test compound is then introduced to the reaction vessel containing the mGluR4 receptor followed by the addition of glutamate. In the alternative the glutamate may be added simultaneously with the test compound. Unbound molecules are washed free and the eluent inspected for the presence of glutamate or the test compound.

For example, in a preferred method of the invention, radioactively or chemically labeled glutamate may be used. The eluent is then scored for the chemical label or radioactivity. The absence or diminution of the chemical label or radioactivity indicates the formation of the glutamate/mGluR4 receptor complex. This indicates that the test compound has not effectively competed with glutamate in the formation of the glutamate/mGluR4 receptor complex. The presence of the chemical label or radioactivity indicates that the test compound has competed with glutamate in the formation of the glutamate/mGluR4 receptor complex. Similarly, a radioactively or chemically labeled test compound may be used in which case the same steps as outlined above would be used except that the interpretation of results would be the converse of using radioactively or chemically labelled glutamate.

As would be understood by the skilled artisan, these assays may also be performed such that the practitioner measures the radioactivity or chemical label remaining with the protein, not in the eluent. A preferred such assay employs radiolabeled glutamate. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The mGluR4 receptor may be free in solution or bound to a membrane. Whether the mGluR4 receptor is bound to a membrane or is free in solution, it is generally important that the conformation of the protein be conserved. In a preferred practice of the invention, therefore, the mGluR4 receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to mGluR4 receptor, because skilled artisans will recognize that any information regarding binding or selectivity of a particular compound is beneficial in the pharmaceutical development of drugs.

In one such competition assay, a battery of known glutamate receptor antagonists, agonists, and partial agonists are evaluated for their relative abilities to inhibit the binding of [$^3$H]glutamate to the human mGluR4 receptor of the present invention.

In this assay cells stably expressing the cloned human mGluR4 receptor are harvested by centrifugation at 2200×g for 15 minutes at 4° C. Membranes for the binding assays are prepared by vortexing the cell pellet in 50 mM Tris.HCl, pH 7.4 (0.5×10$^9$ cells/30 ml). The tissue suspension is then centrifuged at 39,800×g for 10 minutes at 4° C. This procedure is repeated for a total of three washes, with a 10 minute incubation at 37° C. between the second and third washes. The final pellet is homogenized in 67 mM Tris.HCl, pH 7.4, at 12.5×10$^6$ cells/ml using a TISSUMIZER® (Tekmar, Cincinati, Ohio) at setting 65 for 15 seconds.

Binding assays are performed in triplicate in 0.8 ml total volume. Volumes of 200 μl of membrane suspension (0.07–0.10 mg of protein) and 200 μl of drug dilution in water are added to 400 μl of 67 mM of Tris-HCl, pH 7.4, containing [$^3$H]glutamate (35 nM final concentration, 23.7 Ci/mole), calcium chloride (3 mM), pargyline (10 μM), and L-ascorbic acid (5.7 nM). The reaction mixtures are incubated at 37° C. for 15 minutes and then rapidly filtered, using a BRANDEL™ cell harvester (Model MB-48R; Brandel, Gaithersburg, Md.) over Whatman GF/B filters that had been presoaked in 0.5% polyethyleneimine and precooled with ice-cold 50 mM Tris.HCl, pH 7.4. The filters are then washed rapidly times with ice-cold (4×1 ml each).

The amount of [$^3$H]glutamate trapped on the filters is determined by liquid scintillation counting. For the competition experiments, six concentrations of displacing drugs are used, ranging from 10$^{-5}$ to 10$^{-10}$ M. The IC$_{50}$ values are determined by nonlinear regression analysis (SYSTAT™; Systat Inc., Evanston, Ill.) which may be converted to $K_i$ values using the Cheng-Prusoff equation. Y. Cheng and W. H. Prusoff, *Biochemical Pharmacology*, 22:3099–3108 (1973).

In this particular type of competition assay the following compounds are frequently used.

(a) Quisqualate—a compound of the formula

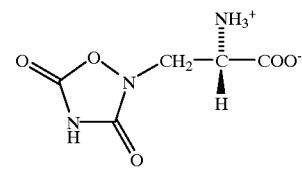

having the chemical name (S)-α-amino-3,5-dioxo-1,2,4-oxadiazolidine-2-propanoate. This compound can be prepared as described in J. E. Baldwin, et al., *Chemical Communications*, 256 (1985).

(b) Glutamate—a compound of the formula

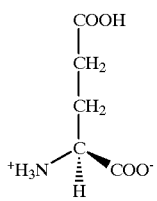

having the chemical name 1-aminopropane-1,3-dicarboxylic acid. This compound is readily available and can be purchased commercially from several sources.

(c) Ibotenate—a compound of the formula

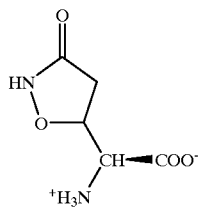

having the chemical name α-amino-3-hydroxy-5-isoxazoleacetate, which can be prepared as described in U.S. Pat. No. 3,459,862, herein incorporated by reference.

(d) t-ACPD—a compound of the formula

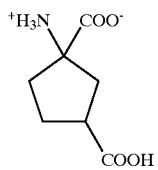

having the chemical name 1-aminocyclopentane-1,3-dicarboxylic acid. This compound can be purchased commercially from several sources.

(e) (2R,4R) 4-amino-pyrrolidine-2,4-dicarboxylic acid, a compound of the formula

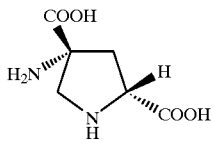

which is described in co-pending U.S. Pat. No. 5,473,077. Many 1-substituted derivatives of this dicarboxylic acid are also effective as mGluR4 antagonists.

The previously described screening system identifies compounds which competitively bind to the mGluR4 receptor. Determination of the ability of such compounds to stimulate or inhibit the action of the mGluR4 receptor is essential to further development of such compounds for therapeutic applications. The need for a bioactivity assay system which determines the response of the mGluR4 receptor to a compound is clear. The instant invention provides such a bioactivity assay, said assay comprising the steps of:

a) transfecting a mammalian host cell with an expression vector comprising DNA encoding a mGluR4 receptor;

b) culturing said host cell under conditions such that the mGluR4 receptor protein is expressed, c) exposing said host cell so transfected to a test compound, and d) measuring the change in a physiological condition known to be influenced by the binding of glutamate to the mGluR4 receptor relative to a control in which the transfected host cell is exposed to glutamate.

An oocyte transient expression system can be constructed according to the procedure described in S. Lübbert, et al., *Proceedings of the National Academy of Sciences (USA)*, 84:4332 (1987).

In an especially preferred embodiment of this invention an assay measuring the inhibition of forskolin-stimulated cAMP synthesis was performed. The inhibition of cAMP synthesis is known to positively correlated with the addition of glutamate to cells containing certain types of metabotropic receptors.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', $Fab_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., *Science* 242:423–426 (1988); PCT Publication No. WO 88/01649, which was published Mar. 10, 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of mGluR4 receptors.

In addition to being functional as direct therapeutic and diagnostic aids, the availability of a family of antibodies which are specific for the mGluR4 receptor enables the development of numerous assay systems for detecting agents which bind to this receptor. One such assay system comprises radiolabeling mGluR4 receptor-specific antibodies with a radionuclide such as $^{125}I$ and measuring displacement of the radiolabeled mGluR4 receptor-specific antibody from solid phase mGluR4 receptor in the presence of a potential antagonist.

Numerous other assay systems are also readily adaptable to detect agents which bind mGluR4 receptor. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the mGluR4 receptor, this invention also provides antibodies which are specific for the hypervariable regions of the anti-mGluR4 receptor antibodies. Some such anti-idiotypic antibodies would resemble the original epitope, the mGluR4 receptor, and, therefore, would be useful in evaluating the effectiveness of compounds which are potential antagonists, agonists, or partial agonists of the mGluR4 receptor. See. e.g., Cleveland, et al., *Nature (London)*, 305:56 (1983); Wasserman, et al., *Proceedings of the National Academy of Sciences (USA)*, 79:4810 (1982).

In another embodiment, this invention encompasses pharmaceutical formulations for parenteral administration which contain, as the active ingredient, the anti-mGluR4 receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

The following example more fully describes the present invention. Those skilled in the art will recognize that the particular reagents, equipment, and procedures described in the Example is merely illustrative and is not intended to limit the present invention in any manner.

EXAMPLES

I. Preparation of the RGT Cell Line

To construct the RGT cell line of the present invention, cDNA encoding the sodium dependent glutamate/asparate transporter (GLAST) was isolated from lambda ZAP® II cDNA library derived from rat hippocampus (Stratagene, Inc., La Jolla, Calif., Catalog # 936518). The published sequence (see Desai et al, supra) was used to design PCR primers which generated a 602 base pair fragment from an aliquot of the library as template. This fragment was used as template to generate a radioactively labelled probe for screening the cDNA library. Using standard plaque hybridization techniques (moderate stringency, 1 M Na+, 60° C.) a number of positive clones were isolated. By further dilution and hybridization, a phage clone was purified which contained the complete coding sequence for the gene. The plasmid containing the insert was excised from the phage using helper phage and protocols supplied by the manufacturer. The GLAST cDNA from this lambda ZAP®II phage was excised on a pBluescript phagemid vector as described by Stratagene, Inc. (pBluescript® SK+).

The GLAST cDNA was removed from the phagemid on a 2.6 kb EcoRV-SmaI restriction fragment and XbaI linkers were added to each end. This fragment was introduced into the XbaI site of the mammalian expression vector pRc/RSV to construct pRS151 (Invitrogen, Catalog # V780-20). The GLAST cDNA was then transfected into the AV12 cell line using the calcium phosphate precipitation method (Graham et al, *Virology* 52:456–467 (1973)) with reagents obtained from Stragagene, Inc. Ten micrograms of plasmid were used without carrier DNA for each 10 cm petri plate of cells at approximately 50% confluancy. Clones expressing GLAST were selected by resistance to G418 (500 ug/ml)(GIBCO-BRL). Clone RGT was found to accumulate less than 3 micromolar glutamate in culturecompared with parent AV12 at 100 micromolar after 24 hours growth.

II. Isolation and Characterization of the CDNA Encoding the Human mGluR4 Gene A cDNA clone encoding the human mGluR4 gene was isolated from the human cerebellum cDNA library (commercially available from Stratagene, Inc., La Jolla, Calif., Catalog #935201) by hybridization with a $^{32}$P labeled human mGluR4 probe as follows:

A. Design of Primers and Preparation of $^{32}$P-labeled Human mGluR4 Probe.

A computer-generated alignment of published amino acid and nucleotide sequences of rat mGluR4 showed a number of highly homologous regions with other members of the mGluR family. These homologous regions were avoided in designing the primers for PCR amplification of fragments corresponding to the human mGluR4 gene. By using the human based Codon Usage File from Gene Bank (See R. Lathe et al., *J. Mol. Biol.*, 183:7–12 (1985), and also S. Aota et al., *Nucleic Acids Res.*, 16:r315–402 (1988), the five degenerate oligonucleotides listed below were generated:

4 P 1 :

5'-GGCTGGGCCTGGTGGTGGGCYMGGCTNCC-3' (SEQ ID NO:4);

4P2: 5'-TGGMAARCCCAAGGGYCAYCCCCAYATG-3' (SEQ ID NO:5);

4P3: 5'-GGTGATSATGGGSGGGCCSCCNGWNCC-3' (SEQ ID NO:6);

4P4: 5'-CACCTCCTCMAGSCKCAGCACRGGNGC-3' (SEQ ID NO:7); and

4P5: 5'-TTGATGTGGCTKCCCTTCTTSAGNGCRTG-3' (SEQ ID NO:8)

where R=A or G, Y=C or T, M=A or C, K=G or T, S=G or C, W=A or T, and N=A or C or G or T.

These degenerate oligonucleotides were synthesized by the phosphoramidite method on a DNA synthesizer (Applied Biosystems, model 380B) and purified by polyacrylamide gel electrophoresis. For PCR amplification, the oligonucleotides were paired in six combinations (4P1+4P3, 4P1+4P4, 4P1+4P5, 4P2+4P3, 4P2+4P4, 4P2+4approximately 420 bp, 980 bp, 1160 bp, 350 bp, 900 bp and 1080 bp DNA fragments corresponding to the human mGluR4 gene.

The PCR reaction mixtures (50 µl) each contained: 10 µl of 5×PCR buffer (50 m4 Tris-HCl pH 8.5, 150 mM KCl, 15 mM MgCl$_2$ and 0.005% gelatin); 10 µl of 2 mM dNTP mixture (dNTP=dATP+dTTP+dGTP+dCTP); 2 µl of Primer Mix (20 pmoles each); 2 µl of human cerebellum cDNA (Stratagene, Inc., La Jolla, Calif., Catalog # 935201) as template; 0.3 µl (1.5 units) of TaQ Polymerase (GIBCO/BRL, Gaithersburg, Md., Catalog # 18038–042); and 26 µl of autoclaved distilled water. The contents of each tube was mixed, overlayed with 50 µl of mineral oil, and then incubated in a DNA thermal cycler 480 (Perkin Elmer, Norwalk, Conn.) at 95° C. for 5 minutes. Amplification was performed using the following conditions: 1 min. denaturing at 94° C.; 1 min. annealing at 50° C.; and 3 min. extension at 72° C. for a total of 40 cycles. The incubation was continued at 72° C. for 7 minutes. The mixture was then maintained at 4° C. until used. After the cycle was completed, a portion (15 µl) of the reaction mixture was analyzed by agarose (1%) gel electrophoresis and the DNA bands visualized by ethidium bromide staining.

Of the six primer pairs used, one oligonucleotide pair (4P1+4P3) yielded approximately a 420 bp fragment containing mGluR4 specific sequences. This fragment was further amplified using primer pairs 4P2 and 4P3. The resulting 355 bp fragment was cloned into pCR-Script® SK(+) plasmid (Stratagene, Inc., La Jolla, Calif., Catalog #21190) at the SrfI restriction site according to the procedures recommended by the vendor. About 12 white transformants were picked. Each was grown in 3 ml TY media containing 100 µg/ml ampicillin. Plasmids were isolated from these cultures using the QIA$_{prep}$ Spin Plasmid Miniprep Kit (Quiagen, Inc., Chatsworth, Calif., Catalog # 27104). DNA sequence analysis of the insert confirmed the presence of human mGluR4 specific sequences in the amplified PCR product.

To prepare a $^{32}$P-labeled probe, the plasmid DNA containing the above PCR product was used as a template under the following conditions. The mixture (40 µl) contained: 4 µl of 10×PCR buffer (100 mM Tris-HCl pH 8.3, 500 mM KCl, 1.5 mM MgCl$_2$ and 0.01% gelatin, w/v); 3µl of 0.5 mM nucleotide mixture containing dATP, dTTP, and dGTP; 15 µl (150 µci) of [α-$^{32}$P]dCTP (DuPont, NEN); 2 µl of Primer Mix (40 pmoles of 4P2 and 4P3); 1 µl of plasmid DNA (50 ng); 0.3 µl (1.5 units) of TaQ Polymerase; and 15 µl of autoclaved distilled water. The amplification conditions were: 30 sec. denaturing at 95° C.; 1 minute annealing at 55° C.; and 2 minutes extension at 72° C. for a total of 30 cycles. The incubation was continued at 72° C. for 7 minutes. The sample was then maintained at 4° C. The amplified radiolabeled probe was purified by a NUC TRAP® probe purification column (Stratagene, Inc., La Jolla, Calif., Catalog # 400701) and stored at 4° C. until used.

B. Screening the CDNA Library:

A human cerebellum cDNA library (λ Zap®II, Stratagene, Inc., La Jolla, Calif., Catalog # 935201) consisting of 2.5×10$^6$ phages was screened by hybridization with the $^{32}$P-labeled mGluR4 probe prepared as described in Section A. Before adding this DNA probe to the filter, the probe was denatured by heating at 100° C. for 10 minutes followed by chilling quickly on ice. The hybridization was carried out at 42° C.for 16 hours in a hybridization buffer containing: 50% Formamide; 5×SSPE (0.75M NaCl, 50 mM NaH$_2$PO$_4$.H$_{20}$, pH 7.4, 5 mM EDTA); 5× Denhardt's Solution (1.0 g Ficoll, 1.0 g Polyvinyl pyrrolidone, 1.0 g BSA—Pentax Fraction V per liter of water); 0.1% SDS; and 100 µg/ml of denatured salmon sperm DNA. The buffer was carefully discarded and the filters were washed in Wash Buffer 1 (2×SSC containing 0.3M NaCl, 0.03M sodium citrate, pH 7.0 and 0.5% SDS) at room temperature followed by Wash Buffer 2 (1×SSC and 0.1% SDS) at 65° C. for 1 hour, respectively. The filters were dried by blotting on Whatman 3M paper at room temperature and then autoradiographed using an intensifying screen to enhance the signal. After developing, the film was aligned with the filters to select positive plaques. Fourteen positive plaques were picked and stored in 1 ml of SM buffer (0.1M NaCl, 0.01M MgSO$_4$.7H$_2$O, 0.035M Tris-HCl (pH 7.5) and 0.05% gelatin). The size of cDNA inserts in these clones were determined by PCR amplification using primers:

4SP-1: 5'-GGGGACATCACACTGGGAGGCCTGT-3' (SEQ ID NO:9);
4SP-3: 5'-CAGCGGACCTCTGTGCCATCCTTCT-3' (SEQ ID NO:10); and
pBSKF: 5'-CCCTCACTAAAGGGAACAAAAGCT-3' (SEQ ID NO:11); or
pBKSR: 5'-CCCCTCGAGGTCGACGGTATCGAT-3' (SEQ ID NO:12). The PCR reaction mixture (50 μl) contained: 10 μl of 5×PCR buffer, 10 μl of 2 mM dNTP mixture, 2 μl of Primer Mix (20 pmoles each), 5 μl of lambda phage template (prepared by mixing 10 μl of phage lysate, 5 μl of 10% Triton X-100, 10 μl of 5×PCR buffer, 25 μl of water and a drop of mineral oil followed by incubation at 95° C. for 10 minutes and then at 4° C. until used), 0.3 μl (1.5 units) of TaQ Polymerase and 24 μl of water. The contents of the tube were mixed, and then amplification was performed by touch down PCR. After incubation at 95_C for 5 minutes, the cycles for amplification were: 30 seconds denaturing at 94° C.; 30 seconds annealing at 65° C.; and 1 minute extension at 72° C. with autodecrease of 0.5° C. per cycle for a total of 20 cycles followed by 30 second denaturing at 94° C.; 30 second annealing at 55° C.; and 1 minute extension at 72° C. for a total of 10 cycles. After amplification, the products were analyzed by 1% agarose gel electrophoresis and three clones (clones #10, #13 and #14) containing an insert of 3.0 Kb were selected for second round screening.

The phages were diluted with SM buffer to obtain about 200 to 1000 plaques per filter (137 mm diameter) and then rescreened by hybridization with $^{32}$P-labeled mGluR4 probe as described above. A single, well isolated positive plaque from each plate was isolated and stored in SM buffer. The cDNA inserts from these phages were then excised in vivo and rescued into pBluescript® SK(-) plasmids according to the protocols recommended by the vendor (Stratagene, Inc., La Jolla, Calif., Catalog #200253). Ten to twelve white transformants were picked and grown in 3 ml of TY media containing 100 μg/ml of ampicillin. Plasmids were isolated from these cultures using the WIZARD™ Minipreps DNA Purification System (Promega Corporation, Madison, Wis., Catalog # A7100) and analyzed for the presence of cDNA inserts after digestion with EcoRI restriction enzyme by agarose (1%) gel electrophoresis. Those plasmids containing 3.0 Kb inserts were selected for further characterization by DNA sequence analysis. One of the clones, designated pBlue.mGluR4 clone #13, contained a partial coding sequence for mGluR4 with an entire 3'-end and 3'-untranslated region but lacking 180 nucleotides at the 5'-end including start codon ATG. Another clone, designated pBlue.mGluR4 clone #10 also contained a partial coding sequence for mGluR4 gene, lacking 100 nucleotides at the 3'-end and 80 nucleotides at the 5'-end including start codon ATG. The third clone, designated pBlue.mGluR4 clone #14 contained only 210 nucleotides with the start codon ATG corresponding to the 5'-end of the coding region and 25 nucleotides corresponding to the 5'-untranslated region while the rest of the sequences were not related to the mGluR family. The partial sequences of mGluR4 gene in these three clones were manipulated as described below to obtain a full length coding region of mGluR4.

III. Construction of Plasmid pBLUE.mGluR4S1

Two approaches (designated below as A and B) were taken to fuse partial nucleotides sequences of mGluR4 present in the plasmids pBlue.mGluR4 clones #10, #13 and #14 to obtain a full length cDNA encoding human mGluR4 gene.

Method A

A 375 bp XhoI restriction fragment corresponding to the 5'-end of mGluR4 was first generated by PCR with primers:
4-SP3: 5'-CAGCGGACCTCTGTGCCATCCTTCT-3' (SEQ ID NO:13)
4-SP9: 5'-GGGCTCGAGGTCGACGGGTCTCTAGGCCTTTCCG-3' (SEQ ID NO:14) and
human cerebellum single stranded cDNA as a template. The PCR product was then subcloned into plasmid pBlue.mGluR4 clone #13 at the XhoI restriction site to form pBlue.mGluR4S1.

ISOLATION OF A 375 BP XHOI RESTRICTION FRAGMENT

The PCR reaction mixture (100 μl) contained 10 μl of 10×PCR Buffer (100 mM Tris-HCl pH 8.3, 500 mM KCl, 1.5 mM MgCl$_2$, 0.01% w/v gelatin), 2 μl of 2.5 mM dNTP mixture, 2 μl of Primer mix (20 pmoles of 4-SP3 and 4-SP9), 2 μl of human cerebellum single stranded cDNA (Clontech Laboratories, Inc., Palo Alto, Calif. Catalog #7314-1), 0.5 μl (2 units) of TaQ Polymerase and 83.5 μl of water. The amplification conditions were: 1 minute denaturing at 94° C., 1 minute annealing at 50° C. and 2 minutes extension at 72° C. for a total of 30 cycles. The product was purified using WIZARD™ PCR Preps DNA Purification System (Promega Corporation, Madison, Wis., Catalog # A 7170). 20 μl of 10×XhoI buffer (500 mM NaCl, 500 mM Tris-HCl (pH 8.0), and 100 mM MgCl$_2$), 20 μl of 1 mg/ml of BSA, 110 μl water and 5 μl (50 units) of XhoI restriction enzyme (GIBCO/BBL, Gaithersburg, Md., Catalog # 52265A). After gentle mixing, the reaction mixture was incubated at 37° C. for 6–8 hours. The DNA was precipitated with 20 μμl of 1 M NaOAC and 1 ml of ethanol and purified by electrophoresis on a 1% low meling agarose gel. The band corresponding to 375 bp XhoI restriction fragment was sliced from the gel and the DNA recovered using a WIZARD™ PCRpreps DNA Purification System. The fragment was stored in 50 μl of 10 mM Tris-HCl (pH 7.6).

About 10 μl of plasmid pBlue.mGluR4 clone #13 was digested with XhoI restriction enzyme and purified by electrophoresis on a 1% low melting argarose gel as described above. The lareger XhoI restriction fragment was sliced from the gel and the DNA recovered using a QIA$_{quick}$ Gel Extraction Kit (Quiagen, Inc., Chatsworth, Calif., Catalog # 28704). The DNA was stored in 50 μl of 10 mM Tris-HCl (pH 8.5).

About 1 μl of this XhoI restrictin vector was mixed with 4 μl of PCR fragment generated above in a tube containing 1 μl of 10× Ligase buffer (5 PRIME-3PRIME, Inc., Boulder, CO, Catalog # 5301-576246), 1 μl of 50 mM DTT, 1.5 μl of water and 0.5 μl (2 units) of T4 DNA ligase. The reaction mixture was incubated at room temperature for 30 minutes, and then at 65° C. for 10 minutes. The mixture was transformed into Epicurian Coli® XL-Blue Supercompetent Cells (Stratagene, Inc., Lajolla, Calif., Catalog # 200236) according to the protocols recommended by the vendor. The cells were plated on TY-agar plates supplemented with 100 μg/ml ampicillin and the plates were incubated at 37° C. overnight. About twelve white colonies were picked and cultures grown at 37° C. overnight in 3 ml of TY media containing 100 μg/ml ampicillin. Plasmids were isolated from these cultures using a WIZARDT™ Minipreps DNA Purification System (Promega Corporation, Madison, Wis., Catalog # A7100). The presence and orientation of a 375 bp XhoI restriction fragment was determined by PCR with suitable primers:
4-SP7: 5'-GAGCAGGTGTCCAGAATGCGGGCGCCC-3' (SEQ ID NO:15) and T7Primer: 5'-GTAATACGACTCACTATAGGGC-3' (SEQ ID NO:16)

The desired plasmid designated pBlue.mGluR4S1 was further identified by DNA sequence analysis.

Method B

The plasmids pBlue.mGluR4 clone #13, clone #10 and clone #14 containing partial sequences of mGluR4 were cut with appropriate restriction enzymes and the resulting fragments were joined together with TY-DNA ligase to form pBlue.mGluR4S1.

About 10 μg of plasmid pBlue.mGluR4 clone #10 was mixed with 20 μl of 10× NarI bufer (660 mM KOAC, 330 mM Tris acetate (pH 7.9), 100 mM Magnesium acetate, 5 mM DTT), 20 μl of 1 mg/ml BSA, 160 μl of water and 2.5 μl (25 units) of NarI restriction enzyme (Boehringer Mannheim, Indianapolis, Ind., Catalog #1103016). The reaction was incubated at 37_C. for 4 hours and the DNA was precipitated with 20 μl of 3 M NaOAC and 1 ml of ethanol. After centrifugation and drying, the pellet was redissolved in 20 μl of 10× EcoRI buffer (1.0 M NaCl, 0.5 M Tris-HCl (pH 8.0), 100 mM $MgCl_2$), 20 μl of 1 mg/ml BSA, 160 μl of water and 2.5 μl (25 units) of EcoRI restriction enzyme and incubated at 37° C. for 2 hours. The DNA was precipitated and then purified by electrophoresis on a 1% low melting agarose gel. A 184 bp NarI-EcoRI restriction fragment was sliced from the gel and the DNA was recovered by using a WIZARD™ PCRpreps Purification System. The fragment was stored in 50 μl of 10 mM Tris-HCl (pH 7.6).

About 15 μg of plasmid pBlue.mGluR4 clone #13 was digested with NarI restriction enzyme as described previously. After centrifugation and drying, the pellet was redissoved in 20 μl of 10× SalI buffer (1.5 M NaCl, 1.0 M Tris-HCl (pH 7.6, 100 mM $MgCl_2$), 20 μl of 1 mg/ml BSA, 160 μl of water and 3.0 μl (30 units) of SalI resriction enzyme (GIBCO/BRL, Gaithersburg, Md., Catalog #15217-011). The reaction was incubated at 37° C. for 2 hours. The DNA was precipitated and purified by electrophoresis on a 1% low melting agarose gel. A larger NarI-SalI restriction fragment was sliced from the gel and the DNA recovered using a $QIA_{quick}$ Gel Extraction Kit (Quiagen, Inc., Chatsworth, Calif., Catalog # 28704). The vector DNA was stored in 30 μl of 10 mM Tris-HCl (pH 8.5).

A 145 bp SalI-EcoRI restriction fragment was isolated from the plasmid pBlue.mGluR4 clone #14 by PCR with Primers: 4-QP1: 5'CACAGGGCTTGCCCTCTGAGC-3' (SEQ ID NO:17) and 4-SP8: 5'-CGGGTCGACGGGTCTCTAGGCCTTTC-3' (SEQ ID NO:18) as described previously in Method A. The PCR fragment was then treated with SalI and EcoRI restriction enzymes and the resulting product was purified by 1.2% low melting agarose gel electrophoresis. A 145 bp SalI-EcoRI restriction fragment was sliced from the gel and the DNA recovered using a WIZARD™ PCRpreps DNA Purification System and stored in 50 ul of 10 mM Tris-HCl (pH 7.6).

The ligation reaction contained: 1 μl of NarI-SalI vector fragment, 6 μl of 184 bp NarI-EcoRI restriction fragment, and 10 μl of 145 bp SalI-EcoRI PCR fragment, 2.5 μl of 10× ligase buffer, 4.5 μl of water, 1 μl of 1 M DTT and 1 μl (2 units) of TY DNA ligase. After gentle mixing, the reaction mixture was incubated at 4° C. overnight and then transformed into E.coli XL-1Blue competent cells (Stratagene, La Jolla, Calif., Catalog # 200236) according to the protocols recommended by the vendor. Several ampicillin resistant colonies were picked and cultures grown at 37° C. overnight in 3 ml of TY media containing 100 ug/ml ampicillin. Plasmids were prepared from these cultures using a WIZARD™ $PCR_{preps}$ DNA Purification System.

The plasmid pBlue.mGluR4S1 was identified by restriction enzyme analysis and DNA sequence analysis.

IV. Construction of Plasmid pGT-H.mGluR$_4$

The cDNA insert encoding the mGluR4 gene in the plasmid pBlue.mGluR4 was modified at the unique BglII restriction site to contain SalI restriction site and then subcloned into the pGT-h vector to form the pGT-h.mGluR4 plasmid.

A. Construction of Plasmid pBlue.mGluR$_4$S$_2$ and Isolation of SalI Restriction Fragment Containing the mGluR4 Gene About 10 μg of plasmid pBlue.mGluR4S1 was mixed with 20 μl of 10× BglII buffer (1.0 M NaCl, 500 mM Tris-HCl (pH 8.0) and 100 mM $MgCl_2$), 20 ul of 1 mg/ml BSA, 160 ul of water and 2.5 μl (25 units) of BglII restriction enzyme. 200 μl of the mixture was incubated at 37° C. for 2 hours and extracted with 200 μl of phenol followed by chloroform. The DNA was precipitated by adding 20 μl of 3 M NaOAC and 1 ml of ethanol. After centrifugation and drying the pellet was dissolved in 20 μl of 10× dephosphorylation buffer (500 mM Tris-HCl pH 8.5 and 1 mM EDTA), 180 μl of water and 0.5 μl of Alkaline Phosphatase (Boehringer Mannheim, Indianapolis, Ind., Catalog #1097075). The reaction was incubated at 37° C. for 1 hour and then extracted with phenol and chloroform as before. The DNA was precipitated and purified by electrophoresis on a 1% low melting agarose gel. The larger BglII restriction fragment was sliced from the gel and the DNA was recovered using a $QIA_{quick}$ Gel Extraction Kit. This vector DNA fragment was stored in 50 μl of 10 mM Tris-HCl (pH 8.5).

An oligonucleotide, 5'-GATCTGTCGACA-3'(SEQ ID NO:19), was synthesized on a DNA Synthesizer (Applied Biosystems, Foster City, Calif., Model 380B) and phosphorylated according to the teachings of E. L. Brown, et al., Method in Enzymology, 68:109–151 (1979). The phosphorylated oligonucleotide was then self-annealed to form a linker:

5'-GATCTGTCGACA -3' (SEQ ID NO:19) and
3'- ACAGCTGTCTAG-5' (SEQ ID NO:20)

About 5 μl (20 pmoles) of this linker was mixed with 2.0 μl of BglII digested pBlue.mGluR4Sl vector DNA generated above in a tube containing 5 μl of 10× Ligase buffer, 4 μl 10 mM ATP, 0.5 μl 1 M DTT, 29.0 μl water and 0.5 μl (2.5 units) TY-DNA ligase. After gently mixing, the reaction was incubated at 4° C. overnight and then transformed into E.coli XL-1Blue competent cells (Stratagene, Inc., La Jolla, Calif., Catalog #200236) according to the protocols recommended by the vendor. About 12 ampicillin resistant colonies were picked and cultures were grown in 3 ml of TY media containing 100 μg/ml ampicillin. Plasmids were isolated from these cultures using a WIZARD™ Minipreps DNA Purification System. The desired plasmid designated pBlue.mGluR4S2 was identified by SalI restriction enzyme analysis.

About 15 μl of plasmid pBlue.mGluR4S2 was mixed with 20 μl of 10× SalI buffer, 1 mg/ml BSA, 160 μl of water and 5 μl (50 units) of SalI restriction enzyme. The mixture was incubated at 37° C. for 2 hours. The DNA was precipitated, dried and then dissolved in 10× ScaI buffer (500 mM NaCl, 500 mM KCl, 500 mM Tris-HCl (pH 7.4) and 60 mM MgCl2), 20 μl of 1 mg/ml BSA, 160 μl water and 5 μl (50 units) ScaI restriction enzyme. The mixture was incubated at 37° C. for 2 hours and then purified by electrophoresis on a 1.2% low melting agarose gel. The SalI restriction fragment (3061 bp) was sliced from the gel and the DNA recovered using a $QIA_{quick}$ Gel Extraction Kit. The DNA was stored in 50 μl of 10 mM Tris-HCl (pH 8.5).

B. Construction of Plasmid PGT-H and Isolation of SalI Restriction Fragment

The coding sequence was removed from the resulting plasmid on a 3.06 kb fragment and inserted into the mammalian expresssion vector pGT-h (as described hereinbefore) using standard techniques. The mammalian expression vector pGT-h had been modified by replacing the BcII cloning site with a unique SalI site using commercially obtained linkers. About 15 µg of the resulting plasmid pGT-h was mixed with 20 µl of 10× SalI buffer, 20 µl of 1 mg/ml BSA, 160 µl of water and 3 µl (3 units) of SalI restriction enzyme. The mixture was incubated at 37° C. for 2 hours and then extracted with 200 µl of phenol followed by chloroform. The DNA was precipitated, dried and redissolved in 20 µl of 10× Dephosphorylation buffer, 180 µl water and 0.5 µl (5 units) of Alkaline Phosphatase (Boehringer Mannheim, Indianapolis, Ind., Catalog # 1097075). The reaction mixture was incubated at 37° C. for 1 hour. The mixture was then extracted with 200 µl of phenol and chloroform as before. The DNA was precipitated and purified by electrophoresis on a 1% low melting agarose gel. The SalI vector fragment (7.71 kg) was sliced from the gel and the DNA recovered by melting the agarose and passing through an Elutip-d column (Schleicher and Scheull, Keene, N. H., Catalog #NA010/3), After precipitation and drying the DNA was stored in 30 µl of 10 mM Tris-HCl (pH 7.6).

V. Ligation and Transformation

About 1.0 µl of SalI treated vector pGT-h was mixed with 4 µl of SalI restriction fragment produced in Section 2.1 in a tube containing 1 µl of 10× Ligase Buffer (5PRIME-3PRIME Inc., Boulder, Co., Catalog # 5301-576246), 1 µl of 50 mM DTT, 1.5 µl of water and 0.5 µl (2.0 units) of TY-DNA ligase. The reaction mixture was incubated at room temperature for 30 minutes and later at 65° C. for ten minutes. A portion of the mixture was transformed into E.coli® XL1-Blue supercompetent cells (Stratagene, Inc., Lajolla, Calif., Catalog #200236) according to protocols supplied by the vendor. The cells were plated on TY-agar plates supplemented with 100 µg/ml ampicillin and Anplates incubated at 37° C. overnight.

About 96 ampicillin resistant colonies were picked and transferred into a 96 well microtiter plate containing 200 µl of TY media supplemented with 100 µg/ml ampicillin. The cultures were grown overnight at 37° C. with gentle shaking. The presence and orientation of SalI restriction insert in the plasmids harbored by these cells were determined by PCR amplification of the insert with the primers:

4-SP7: 5'-GAGCAGGTGTCCAGAATGCGGGCGCCC-3' (SEQ ID NO:21);

4-SP4: 5'-GTCTGGCTGGCCTTCATCCCCATC-3' (SEQ ID NO:22);

pGT-hP1:
5'-GTCACACCACAGAAGTAAGGTTCCTTCAC-3' (SEQ ID NO:23): and pGT-hP2:
5'-CCTCACTCTCTTCCGCATCGCTGTCTGCGA-3' (SEQ ID NO:24).

Those plasmids containing the correct orientation of the insert were further identified by DNA sequence analysis. One of these plasmids was designated pGT-h.mGluR4. A restriction site and function map of this plasmid is presented in FIG. 1. The cells harboring pGT-h.mGluR4 were grown and plasmid DNA was isolated from a 500 ml culture by the alkaline lysis method and purified by Cesium chloride-ethidium bromide gradient procedure as described in *Molecular Cloning, A Laboratory Manual*, Ed Manialis, T., Fritsch, E. F. and Sambrook, J., Cold Spring Harbor, N.Y., 90–94.

VI. Expression of Human MGLUR4 in Mammalian Cells

Using standard techniques, the plasmid of 10.68 kb was transfected into the RGT cell line by the calcium phosphate precipitation method (see Graham et al, supra) and clones were selected for hygromycin resistance. Clones which expressed human mGluR4 were identified by measuring agonist (t-ACPD) mediated inhibition of forskolin stimulated adenyl cyclase using a commercially available cAMP assay kit.

VII. Adenylate Cyclase Activity

Adenylate cyclase activity was determined in initial experiments in transfected mammalian cells, using standard techniques. See, e.g., N. Adham, et al., supra,; R. L. Weinshank, et al., *Proceedinas of the National Academy of Sciences (USA)*, 89:3630–3634 (1992), and the references cited therein.

Mammalian cells (the cell line RGT was employed here) were stably transfected with the plasmid pGT-h.mGluR4, containing human mGluR4 cDNA inserted in the plasmid vector pGT-h, as depicted in FIG. 1. The cells were maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 µg/ml hygromycin.

For the assay the cells were disassociated from stock culture flasks with trypsin, and planted in 24-well plastic culture dishes (15 mm wells) at a density of 500–700,000 cells per well using the same culture medium. After twenty four hours incubation in a humidified carbon dioxide incubator, the cell monolayers were washed with buffer (Dulbecco's phosphate-buffered saline containing 0.5 mM isobutylmethylxanthine and 3 mM glucose) and then incubated in the same buffer at 37° C. for 30 minutes. The monolayers are then washed four additional times with buffer.

Drugs and forskolin, or forskolin alone, dissolved in buffer, was added after the final wash. After incubating for 20 minutes at 37° C., 0.5 ml of 8 mM EDTA was added to each well. The plates were then placed in a boiling water bath for about four minutes. The supernatant fluids are then recovered from the wells and lyophilized. Cyclic adenosinemonophosphate (cAMP) determinations were carried out on the lyophilized samples using commercially available radioimmunoassay kits, following the manufacturer's instructions. The cAMP level in wells containing drug was compared to the forskolin controls.

What is claimed is:

1. An isolated nucleic acid encoding a polypeptide functional as a human metabotropic glutamate receptor comprising the amino acid sequence of SEQ ID NO:2 wherein said nucleic acid comprises the full nucleotide sequence given by SEQ ID NO:1 or SEQ ID NO:3.

2. A composition comprising a buffer and an isolated nucleic acid containing a sequence encoding a human glutamate receptor as claimed in claim 1, wherein said sequence encoding a human glutamate receptor is selected from the group consisting of:

(a) the full sequence of SEQ ID NO:1; and (b) the full sequence of SEQ ID NO:3.

3. A composition as claimed in claim 2 wherein the isolated nucleic acid is deoxyribonucleic acid.

4. A composition as claimed in claim 2 wherein the isolated nucleic acid is ribonucleic acid.

* * * * *